US 6,398,726 B1

(12) United States Patent
Ramans et al.

(10) Patent No.: US 6,398,726 B1
(45) Date of Patent: Jun. 4, 2002

(54) STABILIZER FOR ROBOTIC BEATING-HEART SURGERY

(75) Inventors: Andris D. Ramans, Mountain View; David J. Rosa, San Jose; Volkmar Falk, Woodside, all of CA (US)

(73) Assignee: Intuitive Surgical, Inc., Mountain View, CA (US)

( * ) Notice: Subject to any disclaimer, the term of this patent is extended or adjusted under 35 U.S.C. 154(b) by 0 days.

(21) Appl. No.: 09/436,524

(22) Filed: Nov. 9, 1999

Related U.S. Application Data

(63) Continuation-in-part of application No. 09/374,643, filed on Aug. 16, 1999, which is a continuation-in-part of application No. 09/399,457, filed on Sep. 17, 1999, and a continuation-in-part of application No. 09/433,120, filed on Nov. 3, 1999
(60) Provisional application No. 60/109,301, filed on Nov. 20, 1998, provisional application No. 60/109,303, filed on Nov. 20, 1998, provisional application No. 60/109,359, filed on Nov. 20, 1998, and provisional application No. 60/150,145, filed on Aug. 20, 1999.

(51) Int. Cl.[7] ................................................ A61B 1/32
(52) U.S. Cl. ........................ 600/229; 600/235; 600/228
(58) Field of Search .............................. 600/201, 227, 600/229, 231–235

(56) References Cited

U.S. PATENT DOCUMENTS

| 5,417,210 A | 5/1995 | Funda et al. |
| 5,676,673 A | 10/1997 | Ferre et al. |
| 5,894,843 A | 4/1999 | Benetti et al. |
| 5,923,770 A | 7/1999 | O'Donnell et al. |
| 5,971,976 A | 10/1999 | Wang et al. .................. 606/1 |
| 6,036,641 A | 3/2000 | Taylor et al. ............... 600/231 |
| 6,102,854 A | 8/2000 | Cartier et al. .............. 600/228 |

Primary Examiner—Gary Jackson
(74) Attorney, Agent, or Firm—Townsend and Townsend and Crew LLP

(57) ABSTRACT

Surgical methods and devices allow closed-chest surgery to be performed on a heart of a patient while the heart is beating. A region of the heart is stabilized by engaging a surface of the heart with a stabilizer without having to stop the heart. Motion of the target tissues is inhibited sufficiently to treat the target tissues with robotic surgical tools which move in response to inputs of a robotic system operator. A stabilizing surface of the stabilizer is coupled to a drive system to position the surface from outside the patient, preferably by actuators of the robotic servomechanism. Exemplary stabilizers includes a suture or other flexible tension member spanning between a pair of jointed bodies, allowing the member to occlude a coronary blood vessel and/or help stabilize the target region between the stabilizing surfaces.

10 Claims, 19 Drawing Sheets

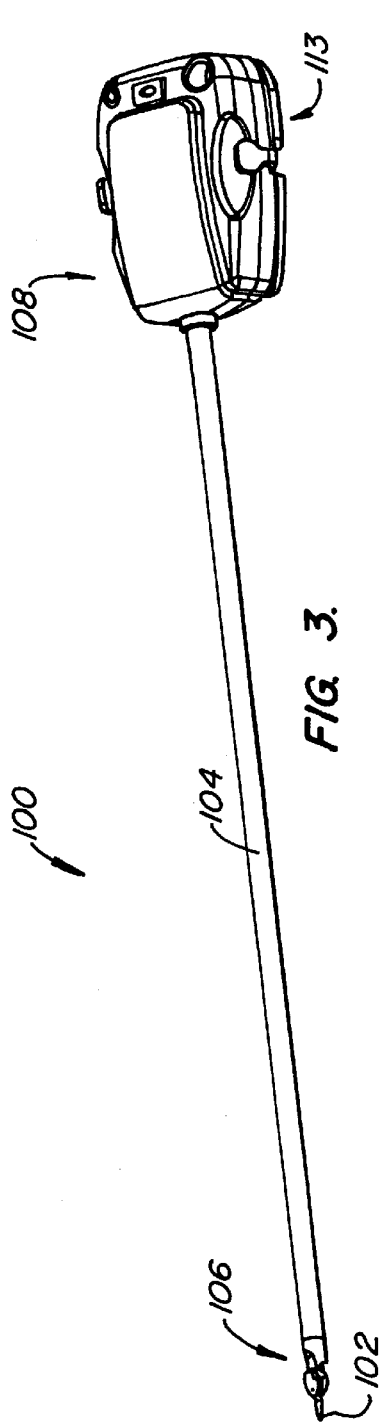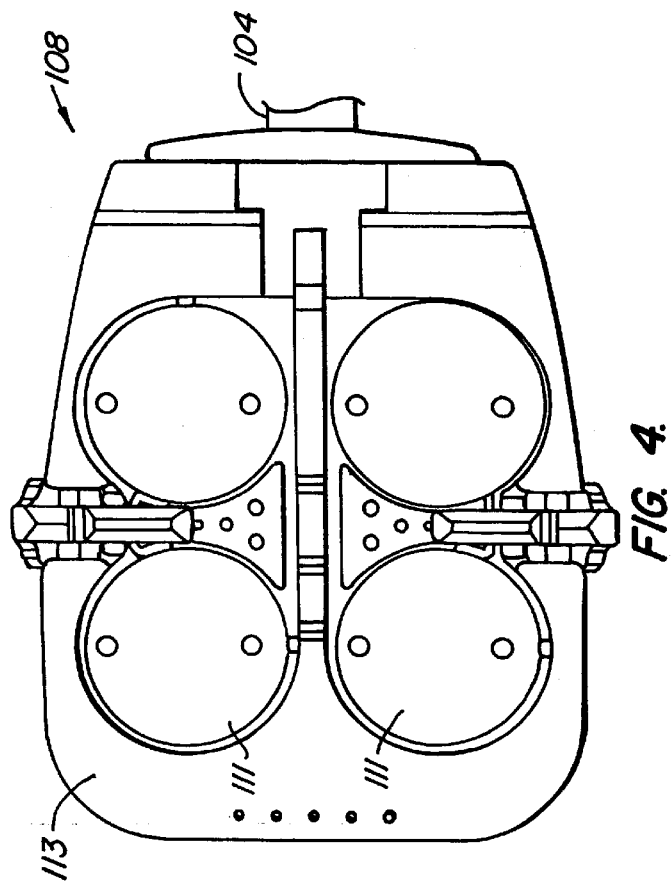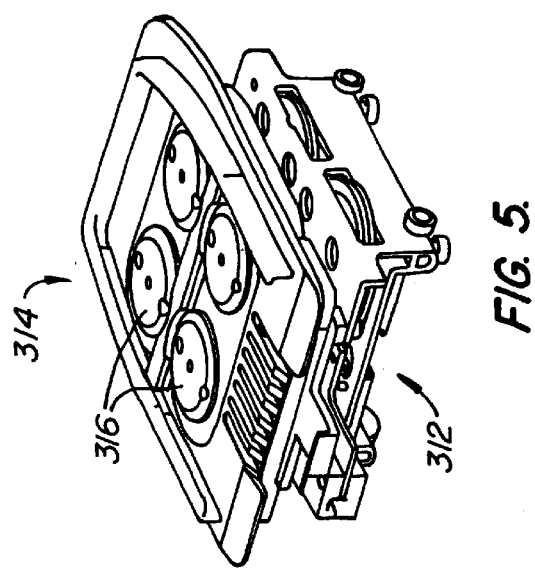
FIG. 3.
FIG. 4.
FIG. 5.

STABILIZER FOR ROBOTIC BEATING-HEART SURGERY

CROSS-REFERENCES TO RELATED APPLICATIONS

The present application is a continuation-in-part of and claims the benefit of priority, from U.S. patent application Ser. No. 09/374,643, filed Aug. 16, 1999, U.S. patent application Ser. No. 09/399,457, filed Sep. 17, 1999, and application Ser. No. 09/433,120, filed on Nov. 3, 1999, each of which is entitled "*Cooperative Minimally Invasive Telesurgical System*", and also claims the benefit of priority from Provisional Application Serial Nos. 60/109,301, filed Nov. 20, 1998, for "*Method for Performing Cardiac Surgery Without Cardioplegia*"; No. 60/109,303, filed Nov. 20, 1998, for "*Apparatus for Performing Cardiac Surgery Without Cardioplegia*"; No. 60/109,359, filed Nov. 20, 1998, for *Apparatus And Method For Tracking And Controlling Cardiac Motion During Cardiac Surgery Without Cardioplegia*"; and No. 60/150,145, filed Aug. 20, 1999, for *Apparatus And Method For Tracking And Controlling Cardiac Motion During Cardiac Surgery Without Cardioplegia*," the full disclosures of which are incorporated herein by reference.

BACKGROUND OF THE INVENTION

This invention generally relates to surgical tools, methods, and systems for stabilizing, retracting, and/or inhibiting physiological movement of tissues. In a particular embodiment, the invention provides a robotic surgical stabilizer for use during robotic surgical treatments on a beating heart.

Coronary artery disease remains the leading cause of morbidity and mortality in western societies. A number of approaches have been developed for treating coronary artery disease. While lifestyle changes, endovascular approaches (such as balloon angioplasty, atherectomy, and the like) and/or pharmaceutical treatments are often effective, in many cases it is necessary to resort to surgical procedures such as coronary artery bypass grafting to effectively treat coronary artery disease.

Coronary artery bypass grafting procedures are commonly performed using open-heart techniques. These open procedures generally involve dividing the patient's sternum and spreading the chest to provide access to the heart. The patient is placed on a heart/lung machine, which oxygenates the patient's blood and pumps it through the circulatory system during the surgical procedure. After the patient is on cardiopulmonary bypass, drugs are administered to temporarily stop the patient's heart (cardioplegia) to allow the grafting procedure to be performed. Typically, a source of arterial blood is connected to a coronary artery downstream from an occlusion, thereby bypassing the occlusion. The source of blood may include the left or right internal mammary artery.

While very effective in many cases, the use of open-heart surgery to perform coronary artery bypass grafting is highly traumatic to the patient. Thus, minimally invasive medical technique for performing cardiac surgeries have recently been proposed. These minimally invasive techniques are generally aimed at reducing the amount of extraneous tissue which is damaged during diagnostic or surgical procedures. This can effectively reduce the patient's recovery time, discomfort, and other deleterious side effects of cardiac surgery. Others have proposed techniques and devices for performing open surgery on a heart while the heart is beating. These proposals generally involve stabilizing a region of the heart by engaging the heart with a tool called a stabilizer. Unfortunately, the proposed techniques for both minimally invasive cardiac surgery and beating-heart cardiac surgery significantly increase the difficulty of these already complex surgical procedures. Formation of the anastomosis (the connection between the arterial source and the occluded artery) is quite challenging in a standard coronary artery bypass grafting procedure when the heart tissues are immobile and exposed for direct manipulation. Even skilled surgeons may find it awkward and/or time consuming to instead perform such procedure in a minimally invasive manner or while the heart is beating.

In robotically assisted surgery, the surgeon typically operates one or more master controllers to remotely control the motion of surgical instruments at the surgical site. The controller may be separated from patient by a significant distance (for example, across the operating room, in a different room, or in a completely different building than the patient). Alternatively, the surgeon's work station with the controllers may be positioned quite near the patient in the operating room. Regardless, the controller will typically include one or more hand input devices, such as a joystick, exo-skeletal gloves, or the like.

The hand input devices of the surgeon's workstation are generally coupled to the surgical instrument by a servo-mechanism. More specifically, servomotors move a manipulator, or "slave" supporting the surgical instrument based on the surgeon's manipulation of the hand input devices.

During a robotic surgical operation, a surgeon using a robotic surgical system may employ, via the manipulator, a variety of surgical instruments, such as tissue graspers, needle drivers, electrosurgical cautery probes, and the like. Each of these structures perform functions for the surgeon, for example, holding or driving a needle, grasping a blood vessel, dissecting, cauterizing, and/or coagulating tissue, and the like. The surgeon and/or an assistant will mount robotic surgical instruments having suitable end effectors to the manipulator, and will often pass the end effectors through cannula sleeves to an internal surgical site, so as to treat the targeted tissues while minimizing injury to the adjacent tissue structures.

In light of the above it would be desirable to provide improved medical devices, systems, and methods. It would be particularly desirable if these improved techniques facilitated coronary artery bypass grafting and other therapies for tissues which undergo physiological movement. It would further be beneficial to provide robotic tools and robotic surgical techniques for treatment of these tissues so as to take advantage of the recently proposed automated systems to improve the ease and speed with which complex surgeries might be performed, while minimizing the deleterious side effects associated with accessing and/or temporarily inhibiting the motion of the target tissues.

SUMMARY OF THE INVENTION

The present invention provides surgical methods and devices which allow closed-chest surgery to be performed on a heart of a patient while the heart is beating. A region of the heart is often stabilized by engaging a surface of the heart with a stabilizer. The stabilizer can inhibit (i.e., substantially reduce) physiological motion of the stabilized region without having to stop the heart. While the stabilized region will not necessarily be absolutely still, motion of the target tissues can be inhibited sufficiently to treat the target tissues, particularly with robotic surgical tools which move in response to inputs of a robotic system operator. A stabilizing surface of the stabilizer will often be coupled to a drive system to position the surface from outside the patient, preferably by actuators of the robotic servomechanism, although manual manipulation from outside the body to position the stabilizer is also possible. Exemplary stabilizers include one or more sutures or other flexible and/or elastic tension members spanning between a pair of jointed bodies, thereby allowing the member to occlude a coronary blood vessel and/or help stabilize the target region between a pair of separated stabilizing surfaces.

In a first aspect, the invention provides a tissue stabilizer for use with a robotic surgical system to treat a target tissue within a patient body. The robotic surgical system has a plurality of manipulators with actuators for moving surgical end effectors in response to inputs by a system operator into an input device. The tissue stabilizer comprises a shaft having a proximal end and a distal end. A first stabilizer body has a stabilizing surface adapted to engage and inhibit movement of the target tissue. A joint couples the distal end of the shaft to the stabilizer, and a drive system is drivingly coupled to the joint so that the stabilizer body can be moved relative to the shaft from outside the patient body. The drive system may allow the stabilizer surface to be positioned using the actuators of a manipulator.

The drive system may be remotely controlled with master controls manipulated by the surgeon or with a manual control outside the body and manipulated by a surgeon's assistant at the patient's side. Preferably, a wrist assembly couples the stabilizer body to the shaft so as to provide first and second degrees of freedom, with the degrees of freedom often being about perpendicular lateral pivotal axes. An exemplary stabilizer includes first and second stabilizer bodies coupled together at a joint so that first and second stabilizing surfaces preferably remain substantially aligned when the bodies are moved relative to each other by the actuators of the manipulator supporting the proximal end of the shaft.

In another aspect, the invention provides a surgical stabilizer for inhibiting motion of a tissue at a surgical site. A surface bordering the tissue is accessible at a surgical site. The system comprises a first body having a first anchor and a first stabilizing surface adapted to engage the tissue surface to inhibit motion of the tissue. A second body has a second anchor and a second stabilizing surface adapted to engage the tissue surface to inhibit motion of the tissue. The second body is moveable relative to the first body.

A flexible tension member can be attached to the first anchor and to the second anchor to engage the tissue between the first and second stabilizing surfaces. Optionally, movement of the first anchor away from the second anchor tensions the flexible member and can urge the flexible member against a tissue. Alternatively, the two anchors can be positioned relative to one another and then a flexible and/or elastic member can be positioned around the vessel to be occluded and attached to the already positioned anchors. This allows the flexible and/or elastic member to, for example, occlude and isolate a region of a blood vessel between the stabilizer bodies. By including a pair of anchors on each body, the target region of a blood vessel may be isolated from both upstream and downstream blood flow, greatly facilitating performing an anastomosis during a coronary artery bypass grafting procedure, or the like.

In yet another aspect, the invention provides a surgical stabilizer for inhibiting motion of a cardiac tissue accessed via a minimally invasive aperture, wherein a heart surface borders the cardiac tissue. The stabilizer comprises a shaft having a proximal and a distal end. A first elongate body extends from the distal end of the shaft. The first body has a first stabilizing surface adapted to engage the heart surface to inhibit motion of the cardiac tissue. A width extends across the stabilizing surface, and the body has a thickness less than the width, with at least one lateral bend along its length. A second elongate body is pivotally coupled to the first body at a joint adjacent the distal end of the shaft. The second body has a second stabilizing surface adapted to engage the heart surface to inhibit motion of the cardiac tissue. A width extends across the second stabilizing surface, with the thickness again being less than the width. The second elongate body also has at least one lateral bend, so that the bodies cross distally of the joint and along the stabilizing surfaces when the bodies are in a small profile configuration suitable for insertion through the minimally invasive opening.

The bodies may each comprise one or more anchors for anchoring flexible occluding members and may be of different lengths to facilitate occupying the small profile even with the anchors as part of the bodies.

In a method aspect, the invention provides a method for performing a surgical procedure at a target region of a coronary vessel on a beating heart. The method comprises stabilizing a region of the heart by engaging first and second bodies against the heart with the region disposed therebetween. The target region of the coronary vessel is isolated with a flexible member extending laterally across the vessel from the first body to the second body. Upstream and downstream isolation of the target region may optionally be provided by including two flexible members spanning between the bodies, with the members optionally defined by a single continuous suture loop, tape, silastic tubing, or the like, although two or more pieces of such flexible material may also be used.

In another method aspect, the invention provides a method for performing a surgical procedure on a target region of a beating heart. The method comprises introducing a stabilizer through a body wall. Motion of the target region is inhibited by engaging the heart with a stabilizing surface of the stabilizer. An end effector of a robotic surgical tool is also introduced through the body wall. The target region of the heart is treated with the end effector while the heart is beating, and while motion of the target region is inhibited by the stabilizer.

BRIEF DESCRIPTION OF THE DRAWINGS

FIG. 3 is a perspective view of an exemplary surgical robotic tool for use in the system of FIG. 1.

FIGS. 4 and 5 illustrate the interface drive elements of the robotic surgical tool and robotic manipulator arms, respectively.

DESCRIPTION OF THE SPECIFIC EMBODIMENTS

Figure 1:
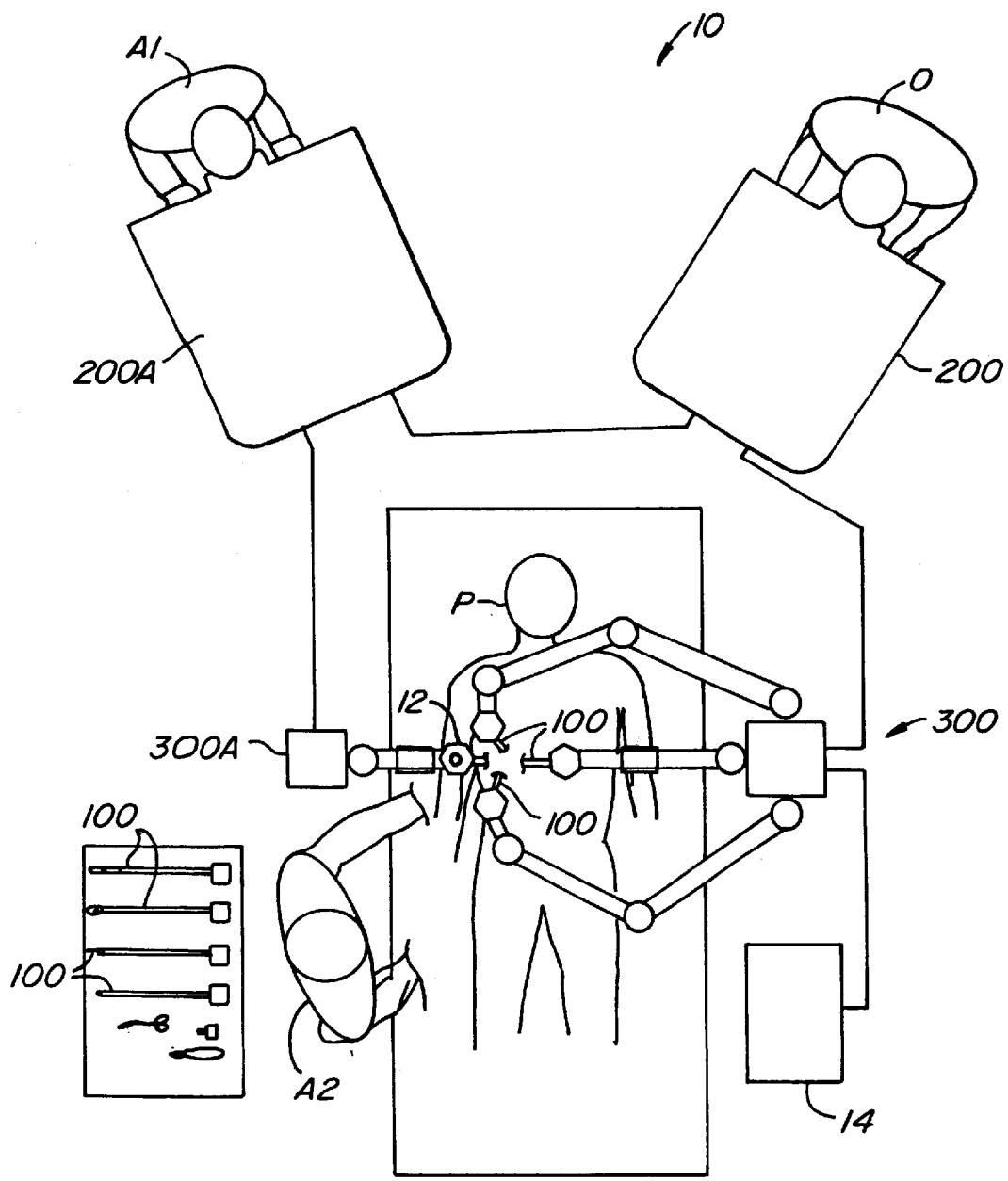
FIG. 1 is a plane view of a telesurgical system and method for performing a robotic minimally invasive surgical procedure.

Referring now to FIG. 1, a robotic surgical system 10 includes a master control station 200 and a slave cart 300. Optionally, any of several other additional components may be included in the surgical system to enhance the capabilities of the robotic devices to perform complex surgical procedures. An operator O performs a minimally invasive surgical procedure at an internal surgical site within patient P using minimally invasive surgical instruments 100. Operator O works at master control station 200. Operator O views a display provided by the workstation and manipulates left and right input devices. The telesurgical system moves surgical instruments mounted on robotic arms of slave cart 300 in response to movement of the input devices. As described in co-pending U.S. patent application Ser. No. 09/433,120, filed on Nov. 3, 1999, the full disclosure of which is incorporated herein by reference, a selectively designated "left" instrument is associated with the left input device in the left hand of operator O and a selectively designated "right" instrument is associated with the right input device in the right hand of the operator.

As described in more detail in co-pending U.S. patent application Ser. No. 09/373,678 entitled "Camera Reference Control in a Minimally Invasive Surgical Apparatus," filed Aug. 13, 1999 (the full disclosure of which is incorporated herein by reference) a processor of master controller 200 will preferably coordinate movement of the input devices with the movement of their associated instruments, so that the images of the surgical tools, as displayed to the operator O, appear substantially connected to the input devices in the hand of the operator.

Optionally, an auxiliary cart A can support one or more additional surgical tools 100 for use during the procedure. One tool is shown here for the illustrative purposes only. A first assistant A1 is seated at an assistant control station 200A, the first assistant typically directing movement of one or more surgical instruments not actively being manipulated by operator O via master control station 200, such as a tissue stabilizer. A second assistant A2 may be disposed adjacent patient P to assist in swapping instruments 100 during the surgical procedure. Auxiliary cart A may also include one or more assistant input devices 12 (shown here as a simple joystick) to allow second assistant A2 to selectively manipulate one or more surgical instruments while viewing the internal surgical site via an assistant display 14. Preferably, the first assistant A1 seated at console 200A has the same image as the surgeon seated at console 200.

As described in U.S. patent application Ser. No. 09/433,120 filed on Nov. 3, 1999, previously incorporated by reference, master control station 200, assistant controller 200A, cart 300, auxiliary cart 300A, and assistant display 14 (or subsets of these components) may allow complex surgeries to be performed by selectively handing off control of one or more robotic arms between operator O and one or more assistants. Alternatively, operator O may actively control two surgical tools while a third remains at a fixed position. For example, to stabilize and/or retract tissues, with the operator selectively operating the retracting or stabilizer only at designated times. In still further alternatives, a surgeon and an assistant can cooperate to conduct an operation without either passing control of instruments or being able to pass control of instruments with both instead manipulating his or her own instruments during the surgery.

Although FIG. 1 depicts two surgeon consoles controlling the two cart structures, a preferred embodiment comprises only one console controlling four or more arms on two carts. The scope may optionally be mounted on the auxiliary cart, and three tissue manipulator arms may be mounted on the main cart. In some embodiments, one or more tools, particularly tissue stabilizers, may not be actively driven, instead being positioned by manually actuating a drive system of the tool and then locking the tool into position.

Figure 2:
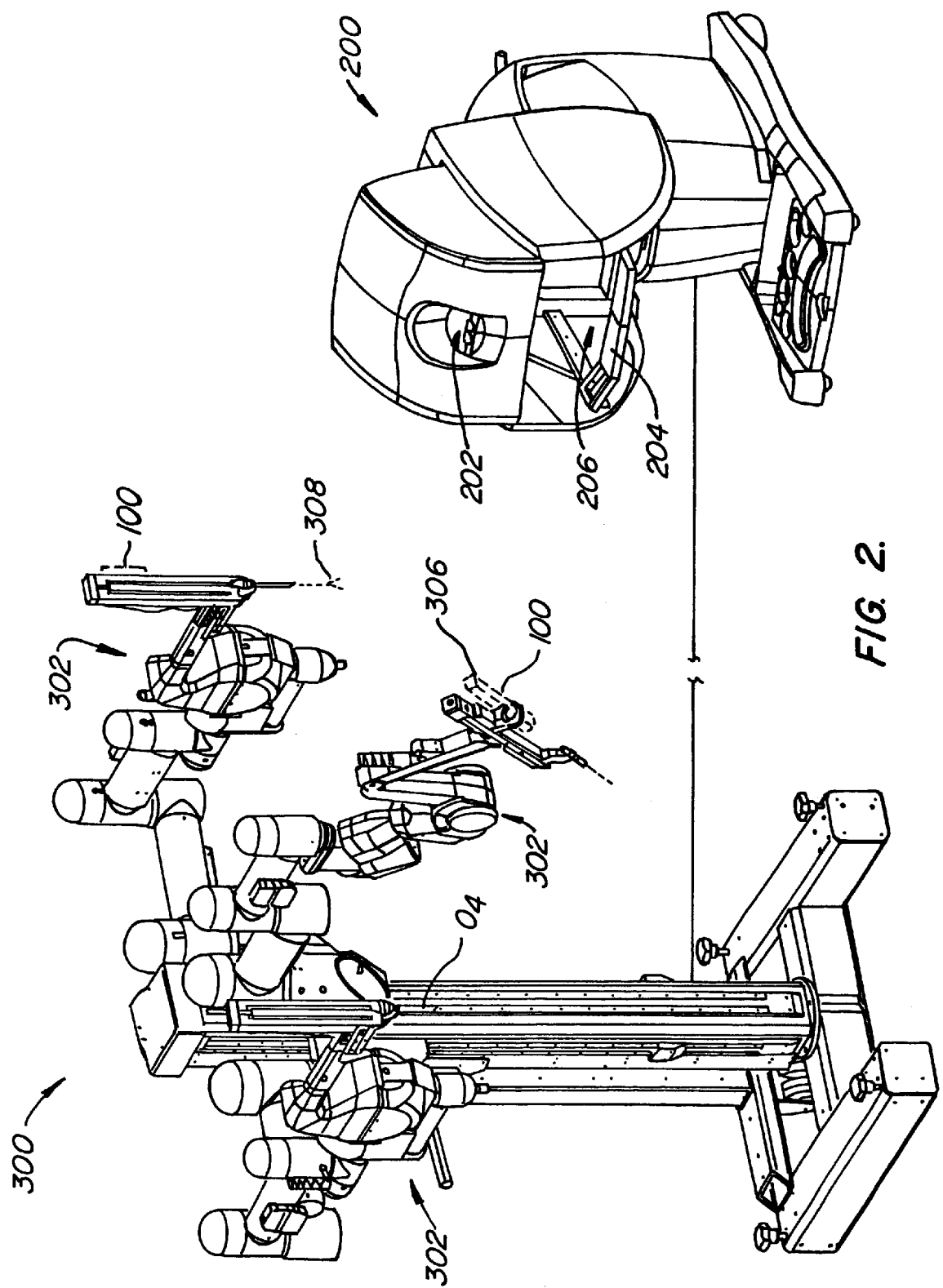
FIG. 2 is a perspective view of a master control workstation and a patient-side cart having three robotic manipulator arms for use in the system of FIG. 1 .

Referring now to FIG. 2, master control station 200 includes a viewer 202 wherein an image of a surgical site is displayed in use. A support 204 is provided on which the operator, typically a surgeon, can rest his or her forearms while gripping two master controls, one in each hand. Master controls are positioned in a workspace 206 disposed inwardly beyond support 204. When using workstation 100, the surgeon typically sits in a chair in front of the workstation, positions his or her eyes in front of the viewer 202 and grips the master controls.

FIG. 2 shows also the surgical manipulator slave or cart 300 of the telesurgical system. In use, cart 300 is positioned close to a patient for surgery, and the base of the cart is caused to remain stationary until the surgical procedure has been completed. Cart 300 here includes three robotic manipulator arm assemblies 302, each manipulator supporting an instrument 100. More specifically, one of the robotic arm assemblies supports an image capture device, such as an endoscope 306 (which is coupled to display 102 of the workstation). Each of the other two manipulator arms supports a tissue manipulation tool 308 having a surgical end effector for treating tissue.

The robotic manipulator arms will move and articulate the surgical tools in response to motions of the input devices at the workstation, so that the surgeon can direct surgical procedures at internal surgical sites through minimally invasive surgical apertures. The workstation 200 is typically used within an operating room with the cart, but can be positioned remote from the cart, even miles away. An exemplary master control input device for manipulation by the surgeon is more fully described in co-pending U.S. patent application Ser. No. 09/398,507, entitled "Master Having Redundant Degrees of Freedom," as filed on Sep. 17, 1999, the full disclosure of which is incorporated herein by reference. Exemplary manipulator arms are more fully described in co-pending U.S. patent application Ser. No. 09/368,309 as filed on Aug. 3, 1999, for a "Manipulator Positioning Linkage for Robotic Surgery," (the full disclosure of which is also incorporated herein by reference), which also describes manually positionable linkages supporting the manipulators. It should be noted that a number of alternative robotic manipulator arms might be used, including those described in U.S. Pat. No. 5,855,583, the full disclosure of which is also incorporated herein by reference.

FIG. 3 shows the general appearance of an exemplary surgical instrument 100 in greater detail. Surgical instrument 100 includes an elongated shaft 104. A joint, preferably in the form of a wrist 106, is located at a distal end of shaft 104. A housing 108 having an interface 113 is disposed at the proximal end of shaft 104, with the interface arranged to releasably couple instrument 100 to the manipulator arm 308.

The structure of interface 113 can be more fully understood with reference to FIGS. 4 and 5. Manipulator arm 302 includes a carriage 312 with a series of drive shafts and electrical connectors for coupling the surgical tool to the workstation 200. To maintain a sterile environment, a drape covers the manipulator arm, and a sterile adaptor 314 is mounted to carriage 312, as more fully described in co-pending U.S. patent application Ser. No. 09/418,726 filed on Oct. 15, 1999, the full disclosure of which is incorporated herein by reference. Sterile adaptor 314 includes a plurality of moveable elements such as rotatable discs 316. These discs are driven by drive elements of carriage 312 and drivingly engage a drive system of the surgical tool, here by rotating drive elements 111 of interface 113.

As more fully described in co-pending U.S. patent application Ser. No. 60/116,844 filed on Jan. 22, 1999, the full disclosure of which is incorporated herein by reference, drive members 111 actuate a drive system of the tool so as to articulate the tool end effectors about two pivotal degrees of freedom of the wrist joint, so as to open and close bifurcated or two piece end effector structures, rotate shaft 104 about its axis, and the like. In the exemplary embodiment, drive members 111 are coupled to pulleys which move cables within shaft 104 and which actuate the end effector elements and pivot the end effector about the wrist joint, as can be understood with reference to FIG. 6.

The wrist mechanism will be described in greater detail with reference to FIGS. 6 and 7. Wrist 106 is disposed at distal end 110 of shaft 104. Wrist mechanism 106 includes a wrist member 112. A proximal end of wrist member 112 is pivotally mounted in a clevis 117 at distal end 110 of shaft 104 by means of a pivotal connection 114. Wrist member 112 can pivot in the direction of arrows 156 about pivotal connection 114.

An end effector, generally indicated by reference 102, is pivotally mounted at a distal end of wrist member 112. The end effector 102 is in the form of, for example, a clip applier for anchoring clips during a surgical procedures, a stabilizer, a needle holder, or the like. In many embodiments, end effector 102 has two elements 102.1 and 102.2, together defining a bifurcated jaw. When a different tool is desired during a surgical procedure, the tool that is then mounted on a manipulator arm may simply be removed by detaching interface 113 from sterile adaptor 314 and replacing the instrument with an alternative instrument bearing the desired end effector, such as scissors, forceps, or the like.

End effector 102 is pivotally mounted in a clevis 119 on distal end of wrist 112 by means of a pivotal connection 160. Elements 102.1, 102.2 can be angularly displaced about pivotal connection 160 toward and away from each other as indicated by arrows 162, 163, and the pivotal connection can also be used to change the orientation of the end effector as a whole relative to wrist member 112.

As shaft 104 is rotatably mounted on housing 108 for rotation, as indicated by arrows 159, end effector 102 has three degrees of freedom of movement relative to the associated manipulator arm 302 in addition to actuation (opening and closing in this example) of the end effector. Namely, rotation about axis 109, angular displacement as a whole about pivot 160, and angular displacement about pivot 114. Other wrist structures and combinations of joints also fall within the scope of the present invention.

The three degrees of freedom of movement of instrument 100 are primarily orientational. This is somewhat a simplification, as movement about these axes will result in some change in position of the end effector. Preferably, manipulator arms 302 will provide at least three primarily translational degrees of freedom for changing a position of the end effector, thereby allowing six full degrees of freedom of the end effector in addition to end effector actuation. The exemplary manipulator arms provide these translational degrees of freedom by pivoting tool 100 about an insertion point into a patient body through a minimally invasive aperture along shaft 104, and by movement of the tool along the shaft through the aperture. Both the orientational movement of the end effector and the translational movement of the robotic manipulator arm can be controlled by actuators such as electrical motors of the manipulator arm, typically in response to input from the associated master control input device. This input will typically comprise a movement of the input device relative to display 102, effecting a corresponding or substantially corresponding movement of the end effector relative to the endoscope. In this specification, actuation or movement of the end effectors relative to each other in the direction of arrows 162, 163, without changing the overall orientation or center line of the end effector 102 is not regarded as a separate degree of freedom of movement.

Figure 8A:
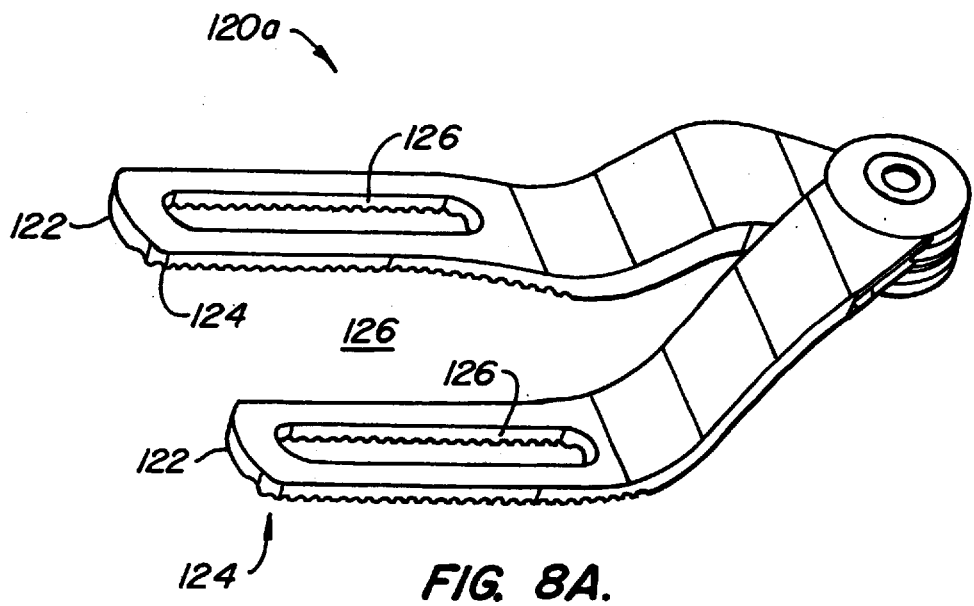
FIGS. 8A–C illustrate alternative end effectors having surfaces for stabilizing and/or retracting tissue.
Figure 8B:
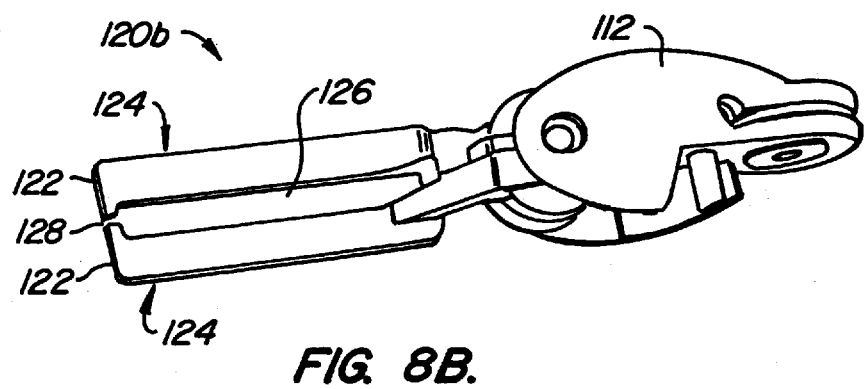
Figure 8C:
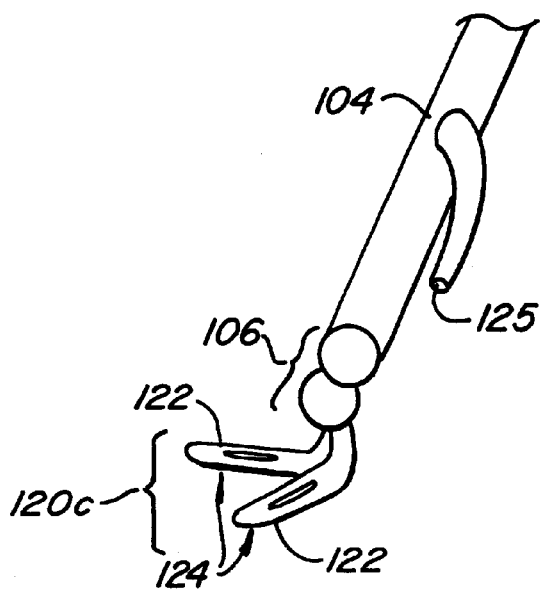

As described above, the end effectors may take a variety of forms to perform different functions within a surgical site. Tissue stabilizer end effectors 120a, 120b, and 120c, referred to generally as tissue stabilizers 120, are illustrated in FIGS. 8A–C. Tissue stabilizers 120 may have one or two end effector elements 122, the elements preferably pivotally attached to the distal end of the shaft or wrist of a surgical instrument and preferably moveable with respect to one another, and preferably comprising tissue-engaging surfaces 124. The tissue-engaging surface features optionally include protrusions, ridges, vacuum ports, or other surfaces adapted so as to inhibit movement between the engaged tissue and the stabilizer, either through pressure applied to the engaged tissue, vacuum applied to draw the tissue into an at least partially stabilized position, or a combination of both pressure and vacuum. The ideal tissue engaging surface will constrain and/or reduce motion of the engaged tissue in the two lateral (sometimes referred to as the X and Y) axes along the tissue-engaging surface, and the stabilizer configuration and engagement with the tissue will at least partially decrease motion normal to the surface. Other configurations for traditional stabilizers are known to those of skill in the art, such as the Octopus II Of Medtronic, Inc. and various Heartport, Inc. and CardioThoracic Systems stabilizers having multipronged and doughnut configurations. These manners of contacting tissue allow stabilizers 120 to firmly engage a moving tissue such as a beating heart of a patient and reduce movement of the tissue adjacent the stabilizer.

To facilitate performing a procedure on the stabilized tissue, an opening 126 may be formed in an individual stabilizer element 122, and/or between independently moveable end effector elements. As illustrated in FIG. 8B, stabilizer 120b includes cooperating tissue grasping surfaces 128 disposed between stabilizer end effector elements 122. This allows the stabilizer to grasp tissues, providing a dual function robotic stabilizer/grasper tool. Stabilizer 120b may be used, for example, as a grasper while harvesting and/or preparing an internal mammary artery (IMA) for a coronary artery bypass graft (CABG) procedure, and/or to hold the IMA during formation of the anastomosis on the stabilized beating heart.

Figure 6:
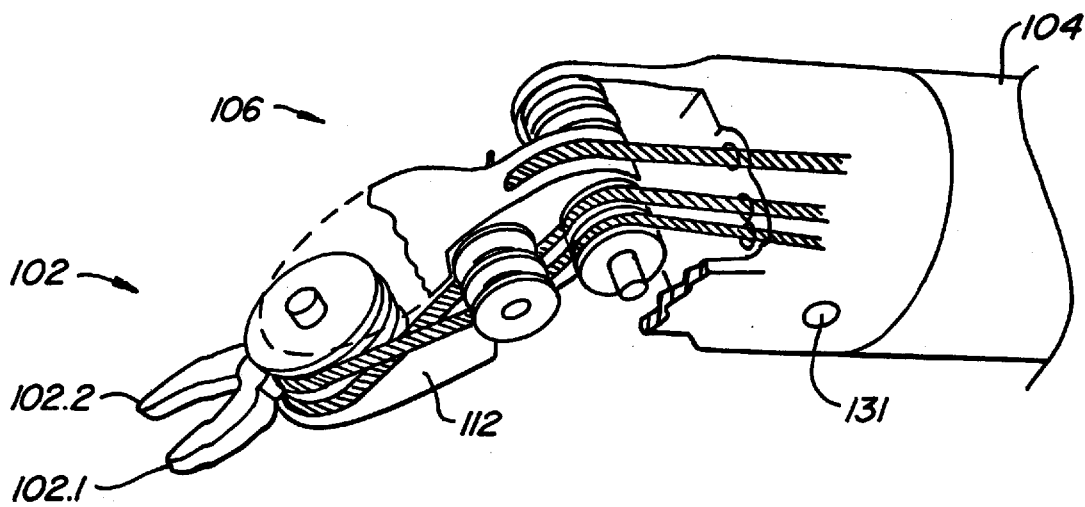
FIGS. 6 and 7 illustrate an exemplary wrist and drive system for positioning end effector elements of the tool of FIG. 3.
Figure 7:
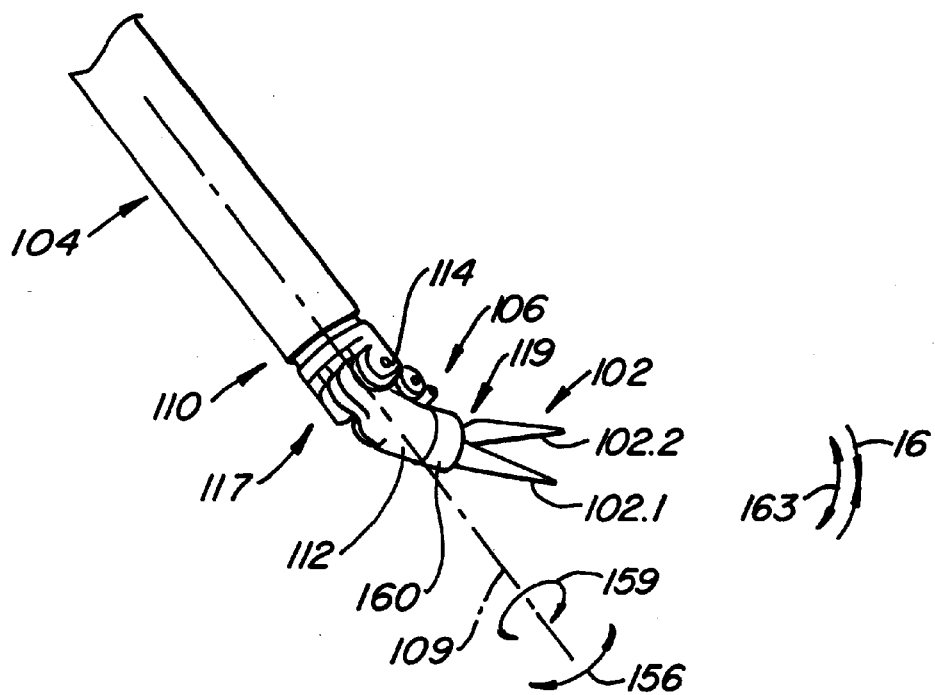

Referring now to FIGS. 6 and 8C, and generally for the robotic endoscopic stabilizers disclosed herein, each stabilizer may comprise an irrigation hose 125 or port 131, the port/hose preferably in fluid communication with a lumen integrated into the shaft of the stabilizer tool The lumen is preferably of a non-crushable material, such as a stainless steel or plastic hypotube, to prevent crimping or crushing by the other internal contents of the system. While an irrigation and/or aspiration capability is particularly beneficial when incorporated into a stabilizer, such capabilities may also be incorporated into the shaft of any robotic surgical tool, as desired, such as other manipulators used during beating heart surgery. The port system, comprising a lumen preferably situated inside the shaft of the stabilizer and extending out of an aperture or port in the distal portion of the shaft, as shown in FIG. 8C, or extending to a port 131 flush with the surface of the wrist mechanism, as shown in FIG. 6, may be used to perform a number of tasks during a surgical procedure (e.g., a beating heart procedure) in which stabilization of tissue or irrigation of the surgical site is desired. Those tasks may include removing undesired fluid from the surgical site (e.g., through suction to outside the patient's body), blowing the fluid into some other portion of the surgical site, and/or delivering fluid (such as spray humidified carbon dioxide or saline) to clear the surgical site of material (such as body fluids which might otherwise interfere with the surgeon's view.) Preferably, at least the distal portion of the port system, shown in FIG. 8C, is flexible to permit bending. The exemplary port structure will be malleable or plastically deformable enough that it will maintain its position for use after being repositioned by another robotic tool or the like.

Figure 9:
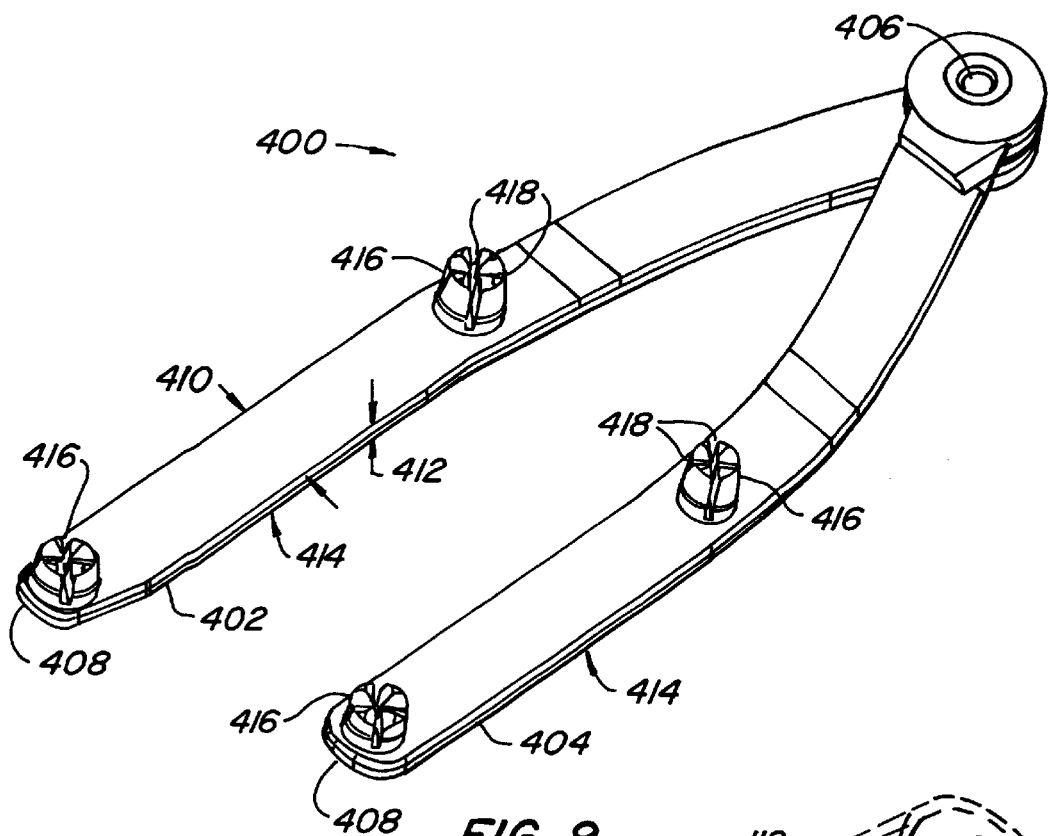
FIG. 9 is a perspective view of a preferred embodiment of the invention showing an exemplary tissue stabilizer end effector formed of pivotally coupled bodies having anchors for affixing tensioned flexible members.
Figure 9A:
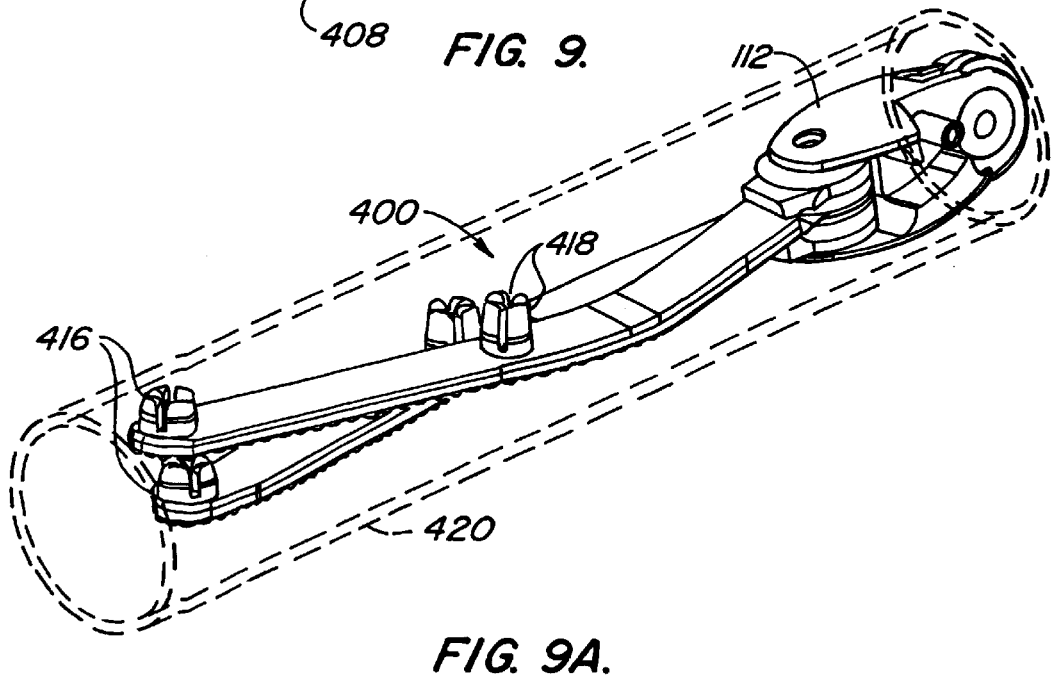
FIGS. 9A–D illustrate the stabilizer of FIG. 9 in a small profile configuration for insertion into an internal surgical site via a cannula.
Figure 9B:
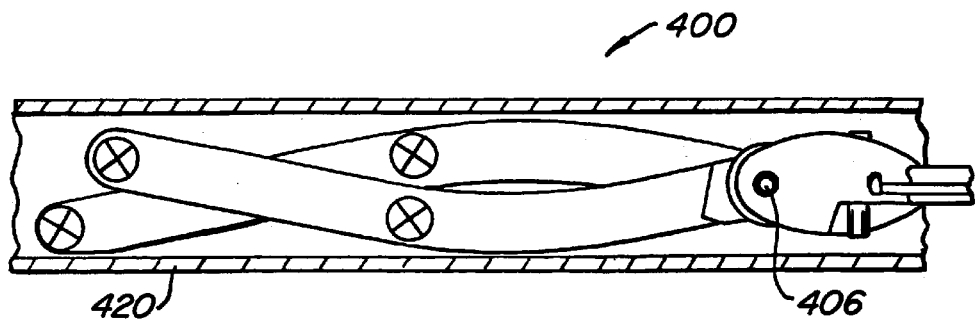
Figure 9C:
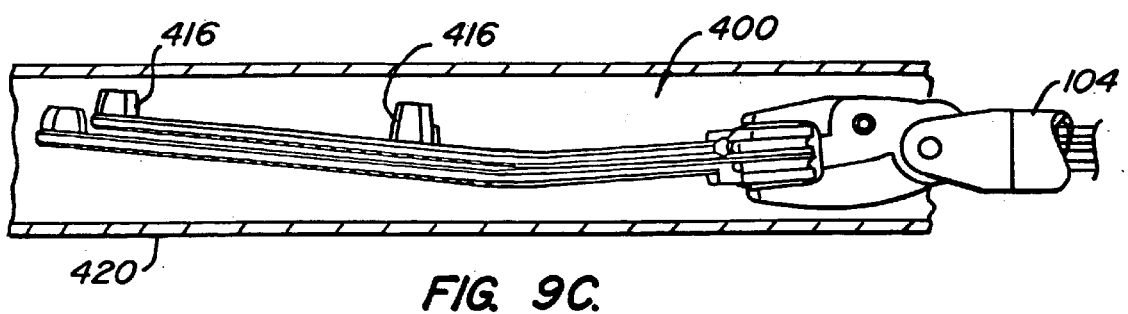
Figure 9D:
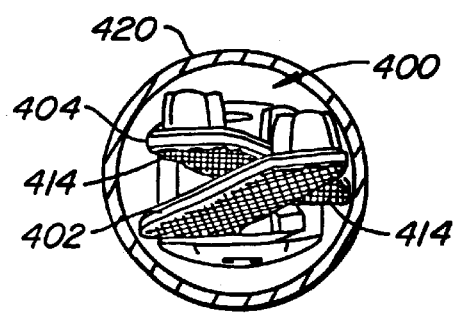
Figure 9E:
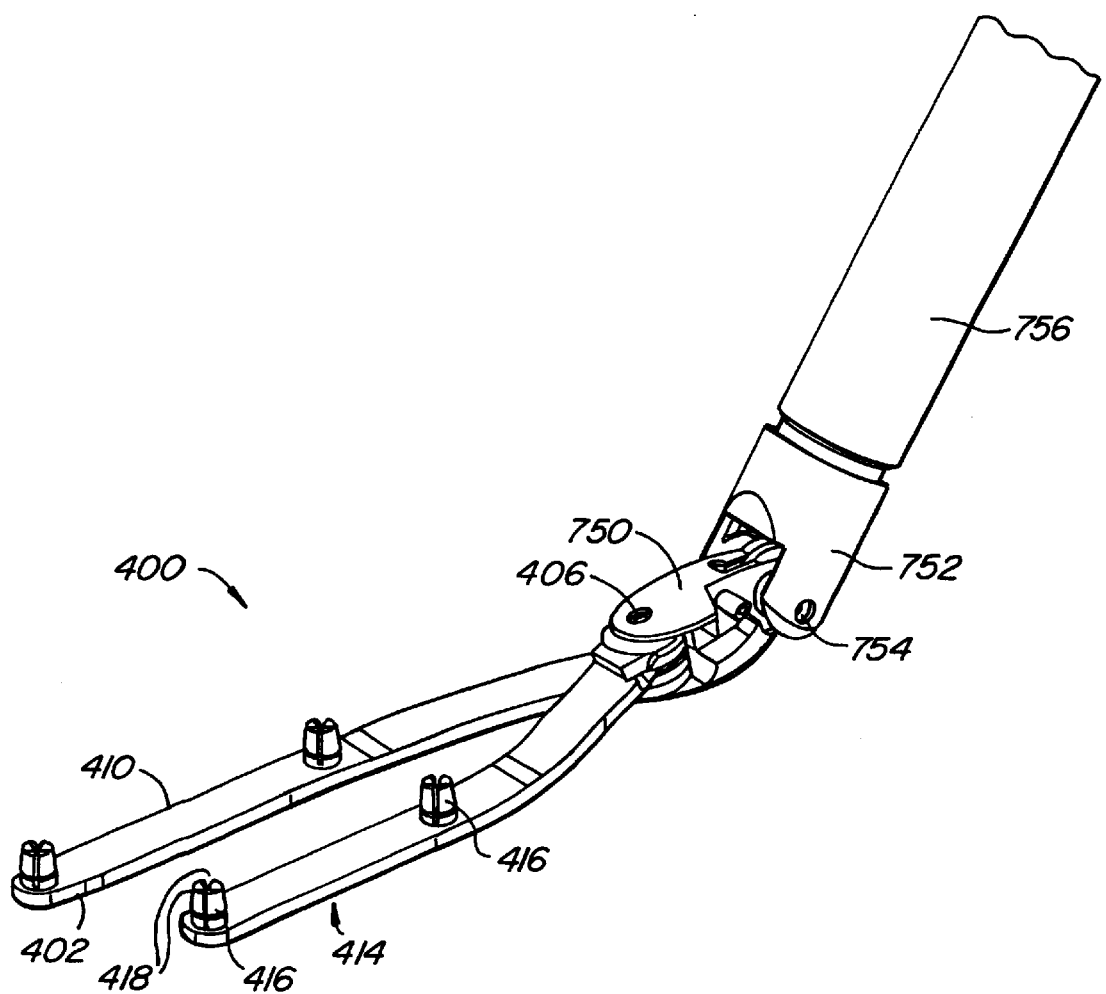
FIG. 9E illustrates an exemplary wrist structure for use with the stabilizer end effector of FIG. 9.

An exemplary stabilizer end effector 400 is illustrated in FIGS. 9 and 9E. Preferred stabilizer 400 generally comprises a bifurcated structure having first and second bodies 402, 404 coupled to each other and to an associated tool shaft 756, wrist, wrist member 112, and the like, at stabilizer pivot 406.

Each of stabilizer bodies 402, 404 comprise an elongate plate extending distally from pivot 406 to a distal end 408. Each plate generally has a width 410 which is less than its length, and thickness 412 preferably less than its width. As can be seen in FIGS. 9B and 9C, each plate preferably bends laterally relative to its length in the direction of its width (so that bodies 402, 404 cross distally of pivot 406 when the stabilizer is in a small profile configuration) and in the direction of its thickness (as shown in FIG. 9C) so that tissue stabilizing surfaces 414 of the bodies can engage a tissue surface without interference from the wrist. Although these multiple bends are preferred, to facilitate better delivery through smaller cannulas and better contact with the heart's surface, these bends should not be understood to limit the scope of the present invention. Pivot 406 preferably maintains general alignment between tissue engaging surfaces 414, and these tissue engaging surfaces will generally be adapted to inhibit relative motion between a tissue engaged by the body and the body surface, such as presenting a textured, knurled, roughened, or other high friction surface, by including one or more vacuum ports, by comprising a high friction material, coating, and/or adhesive, or the like.

The preferred wrist joint structure for the stabilizer 400 is schematically shown in FIG. 9E. Stabilizer end effector 400 is pivotally coupled at pivot 406 to distal clevis structure 750, which in turn is pivotally coupled to proximal clevis 752 at pivot 754. Proximal clevis 752 is constructed to allow the end effector to pivot past 90° to the longitudinal axis of shaft 756. Preferably, the clevis 750 will pivot to at least about 110° or more. This added angular freedom of movement has proven useful in properly positioning the stabilizer during a beating-heart surgical procedure, and can be used with any of the robotic tools disclosed herein. Pivot axes 754 and 406 are preferably substantially orthogonal.

As can be seen in FIGS. 9–9D, protruding anchors or cleats 416 extend away from bodies 402, 404, with the cleats having one or more channels 418 for laterally receiving a flexible member such as a suture, tape, silastic tubing, or the like, and for attaching the flexible member to the body 402, 404 of stabilizer 400. As illustrated in FIG. 9, channels 418 are preferably oriented at about 45° relative to the adjacent edge of body 402, 404 although the angle is not critical. For this angle and two channel, the surgeon has a choice of how to best arrange the silastic tubing with the channels for a particular surgical procedure. Channels 418 in each anchor 416 may be of different sizes to permit different types or sizes of flexible members to be used, and more than two slots may be provided in each anchor. Anchors 416 with channels 418 therein may present an hour glass-like shape to facilitate tying off the flexible member to the anchor. In addition, although two anchors per body are preferred, more than two anchors per body may be included, if desired. Bodies 402, 404 and anchors 416 may comprise a metal, such as 17-4 stainless steel, or a polymer, with the anchors optionally being sufficiently deformable to lock the flexible members into place. When a high strength metal, such as stainless steel, is used, anchors 416 will preferably be electropolished to smooth any rough edges and avoid cutting of the flexible member.

Referring now to FIGS. 9A–D, stabilizer 400 may be configured in a small profile configuration for insertion into an internal surgical site through a minimally invasive aperture, for example, through a cannula 420. Cannula 420 will preferably have a diameter of less than one-half inch, more preferably having an inner diameter of less than 0.4" and ideally having a diameter which tapers slightly from about 0.383" to about 0.343" distally. First body 402 may be longer than second body 404 so as to allow the distal ends 408 of the bodies to cross without interference from cleats 416. Stabilizer 404 may have an overall length from pivot 406 to distal ends 408 of bodies 402, 404 in a range from about 0.75" to about 3.50". More preferably having a length from about 1.0" to 2.5". The plates from which the bodies are formed may have thicknesses of about 0.035", while anchors 416 may protrude by a distance in range from about 0.03" to about 0.15" with the distal anchors optionally protruding less than the proximal anchors to enhance clearance between the stabilizer and the surrounding cannula 420, as shown best in FIG. 9C.

Figure 10A:
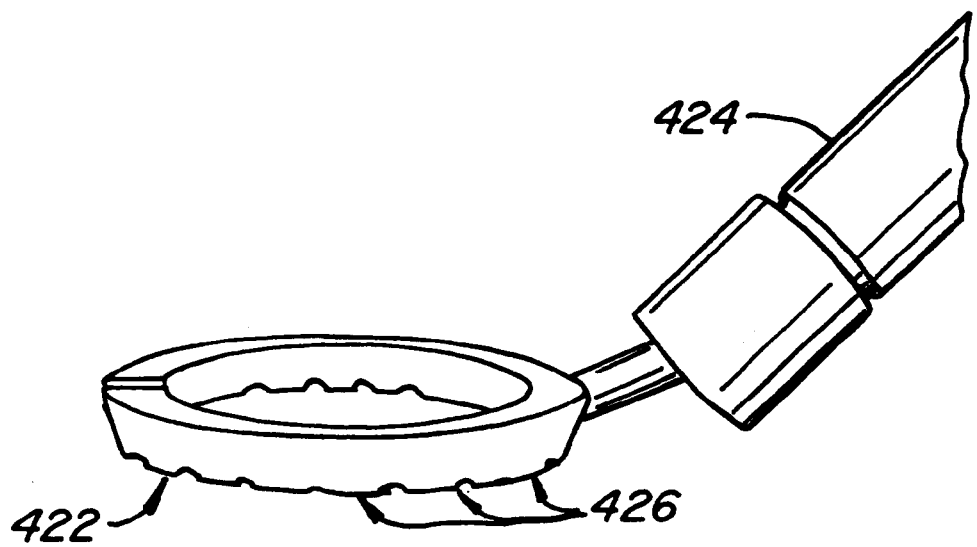
FIGS. 10A–C illustrate known tissue stabilizers.
Figure 10B:
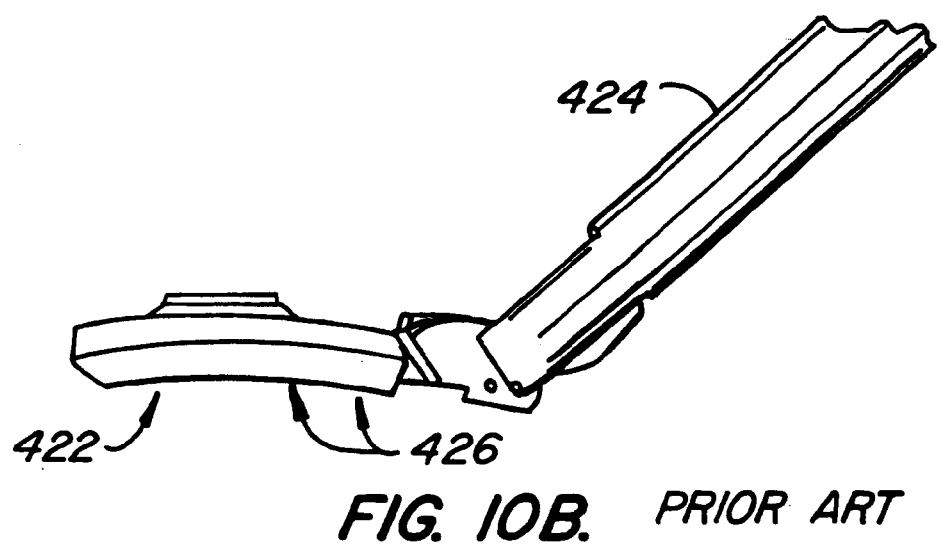
Figure 10C:
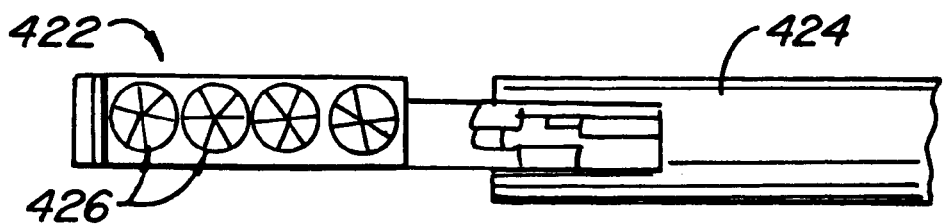

A wide variety of alternative stabilizer structures may also be used within the scope of the present invention, including stabilizer structures similar to those known for use in open surgical procedures. Referring now to FIGS. 10A–C, there can be seen a number of suction-type attachment members 422, which are generally releasably held by a conduit-type attachment arm 424. Attachment arm 424 may be connected to and in communication with a suction hose which communicates with a vacuum or suction source (not shown). FIG. 10A shows a circular-design attachment arm 422 having a plurality of openings 426 wherethrough suction occurs to releasably engage the circular-design attachment arm 422 to the surgical worksite. The known rigid circular-design attachment arm 422 is often unsuitable for insertion through a relatively small cannula because of its shape and size.

FIGS. 10B and 10C show a prior art linear design attachment member 422 having a plurality of openings 426 wherethrough a suction occurs to releasably engage the linear design attachment member 422 to the surgical worksite. The linear design attachment member 422 of FIGS. 10B and 10C may be introduced through a cannula, but may not be capable of surrounding the surgical worksite. Therefore, when such a linear design attachment member 424, as illustrated in FIGS. 10B and 10C is employed, two attachment manipulators may be employed to stabilize the surgical worksite. Alternatively, a V-shaped design attachment member capable of being introduced through a cannula and expanding to surround the surgical worksite, may include a pair of attachment jaws capable of pivoting at a stabilizer pivot point, similar to pivot point 406 of preferred stabilizer 400 (see FIGS. 9 and 13) may be employed. Each of the attachment jaw elements may optionally include a plurality of openings 426 wherethrough suction occurs to releasably engage the V-shaped design attachment member to the surgical worksite. Optionally, the actuated jaws may be spring-loaded to move away from each other when they are clear of the cannula, but the jaws will preferably be directly controlled by an actuator motor of the associated manipulator arm.

Figure 11:
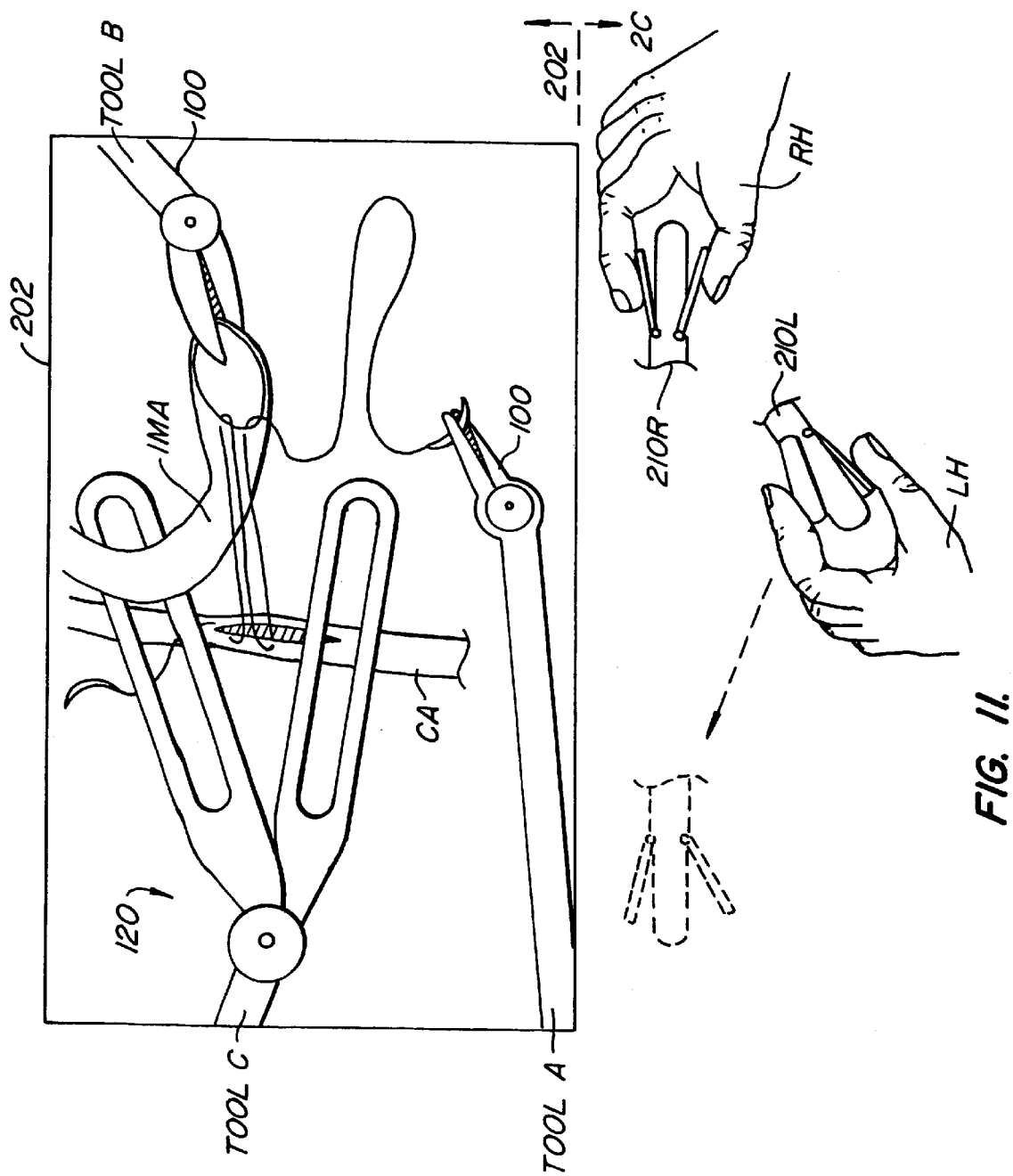
FIG. 11 illustrates a preferred method for performing a coronary artery bypass grafting by manipulating input handles of the robotic surgical system of FIG. 1 with reference to an image of the internal surgical worksite displayed on the master controller workstation.

Referring now to FIGS. 1 and 11, operator O may initially be manipulating tools A and B with input devices 210L and 210R using his or her left and right hands LH and RH, respectively. When the surgeon or operator O intends to maintain control over tool B, but wishes to reposition stabilizer 120, the operator may decouple input device 210L from tool A and instead couple the input device in his or her left hand LH with stabilizer 120 using the tool selection routine described in co-pending U.S. patent application Ser. No. 09/433,120 filed Nov. 3, 1999 entitled "Cooperative Minimally Invasive Robotic Surgery," previously incorporated herein by reference.

Once the selected master input device has been allowed to float, the master may be moved into alignment with the newly selected tool. Often this will occur while the surgeon keeps a hand on the input device, with actuators of the master control station moving the input device at a moderate pace and with moderate force to avoid injury to the surgeon. Master input device 210L may then be coupled to tool C (stabilizer 120 in this example) while tool A is held in a fixed position. This allows the operator to reposition stabilizer 120 against an alternative portion of coronary artery CA. The tool selection process may be repeated to reassociate the masters with tools A and B, while tool C remains held in a fixed position by its drive system. This allows the surgeon to control repositioning stabilizer 120 without significantly interrupting anastomosis of the coronary artery CA with the internal mammary artery IMA. Hence, the system may allow an operator to sequentially control more than two robotic tools using the operator's two hands and the servomechanism of the robotic system. In addition, the stabilizer may be provided with a mechanism to enable the surgeon's assistant to manually move the stabilizer, as desired, during the surgical procedure.

The present invention is particularly useful in performing coronary artery bypass graft (CABG) procedures without cardioplegia. Conventional CABG procedures are described in U.S. Pat. No. 5,452,733 which is fully incorporated herein by reference. Conventional CABG procedures often involve preparing a source of arterial blood for subsequent bypass connection to the narrowed coronary artery at a location beyond the narrowing. Such arterial blood sources will be primarily of two types. First, existing arteries can be dissected from their natural attachments and transected to provide upstream and downstream free ends. The upstream free end, which is the arterial blood source, will be secured to the coronary artery at a location distal to the narrowing, thus providing the desired bypass blood flow. Second, artificial arterial shunts may be prepared by attaching a natural or synthetic blood vessel, typically a length obtained from a leg vein, at one end to the proximal ascending aorta and at the other end to the target location on a coronary artery. The use of transected arteries is generally preferable since they tend to remain patent for long periods and require only one anastomosis.

The arterial blood source will preferably be the left or right internal mammary artery. It will also be possible to use the gastroepiploic artery in the abdomen. Access to the gastroepiploic artery can be obtained laparoscopically, with the artery being brought into the thorax from the abdominal cavity via a window through the diaphragm. When necessary, it will be possible to prepare free grafts from the aorta. Such free grafts can be formed from veins or arteries harvested from other locations in a patient's body, or may comprise synthetic graft materials. The free graft may be passed into the thorax through either an access trocar sheath or through the aorta (by punching a hole therethrough). The free grafts thus located will be attached at one end to the proximal ascending aorta (to provide the arterial blood supply) and at the other end to the target location on the coronary artery.

The left internal mammary artery is suitable as an arterial source for target locations on the left anterior descending coronary artery, the diagonal coronary artery, the circumflex artery/obtuse marginal artery, and the ramus intermedius coronary artery.

The right internal mammary artery is available for connection to all of the same target locations, as well as the right coronary artery and the posterior descending artery. The gastroepiploic artery and free grafts from the aorta will be available for all target locations.

In transecting the left internal mammary artery, the left lung may be deflated and a length of the internal mammary artery dissected from the inner thoracic wall. The side branches of the internal mammary artery are sealed.

Figure 12:
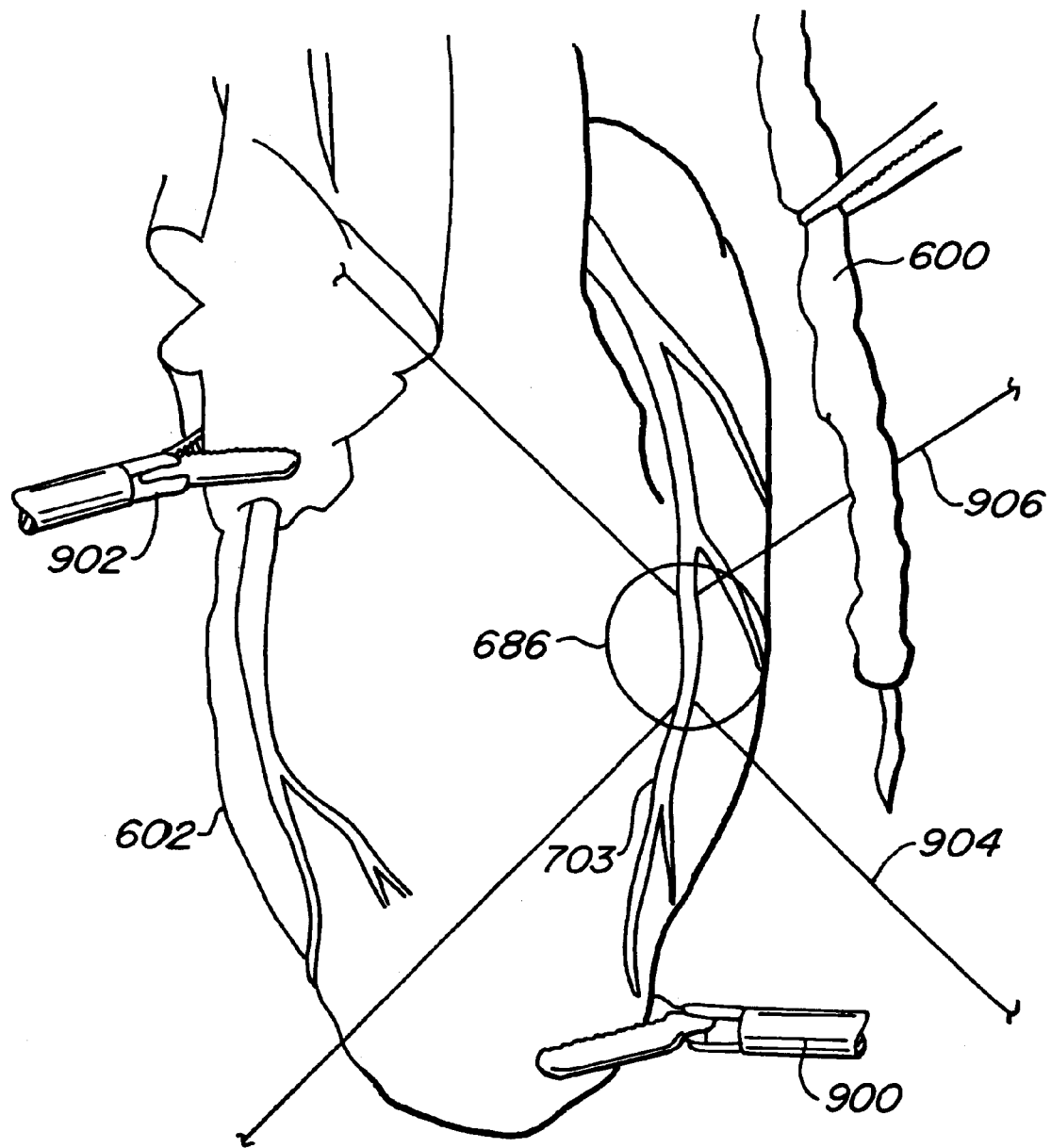
FIG. 12 shows a schematic view of a surgical worksite on a heart prior to a coronary artery bypass graft procedure.

As shown in FIG. 12, the heart 602 will often be repositioned using suitable instruments in order to better expose the coronary artery 703 which is the target for anastomosis in the surgical worksite 686. Suitable instruments include hooks, suction catheters, grasping rods, pushing rods, and the like. Gravity can also be used to help position the heart 602 if the patient can be turned appropriately. As illustrated in FIG. 12, a pair of graspers 900 and 902 may be used to secure opposite sides of the heart 602 and permit turning of the heart 602 as desired. Optionally, trocar sheaths (not shown) may be introduced at other sites of thoracic access. For example, one or more parasternal punctures, one or more punctures in the midclavicular line, and/or a subxyphoid puncture may be introduced.

Elastic members 904 and 906, which are introduced through appropriately positioned trocar sheaths (not shown), often place axial tension on the surgical worksite 686 in the coronary artery 703 which is to be prepared for anastomosis. In addition, they provide a bloodless lumen, permitting excellent visualization. As illustrated in FIG. 12, the coronary artery 703 is first pulled upward from the surface of the heart 602 and stretched using the pair of elastic members 904 and 906.

The surgical worksite 686 in the coronary artery 703 is designated for anastomosis. The motion of the surgical worksite 686 is preferably inhibited by engaging a surface of heart 702 with stabilizer 120, 400. It should be understood that the stabilizer need not completely prevent motion of surgical site 686.

Figure 13:
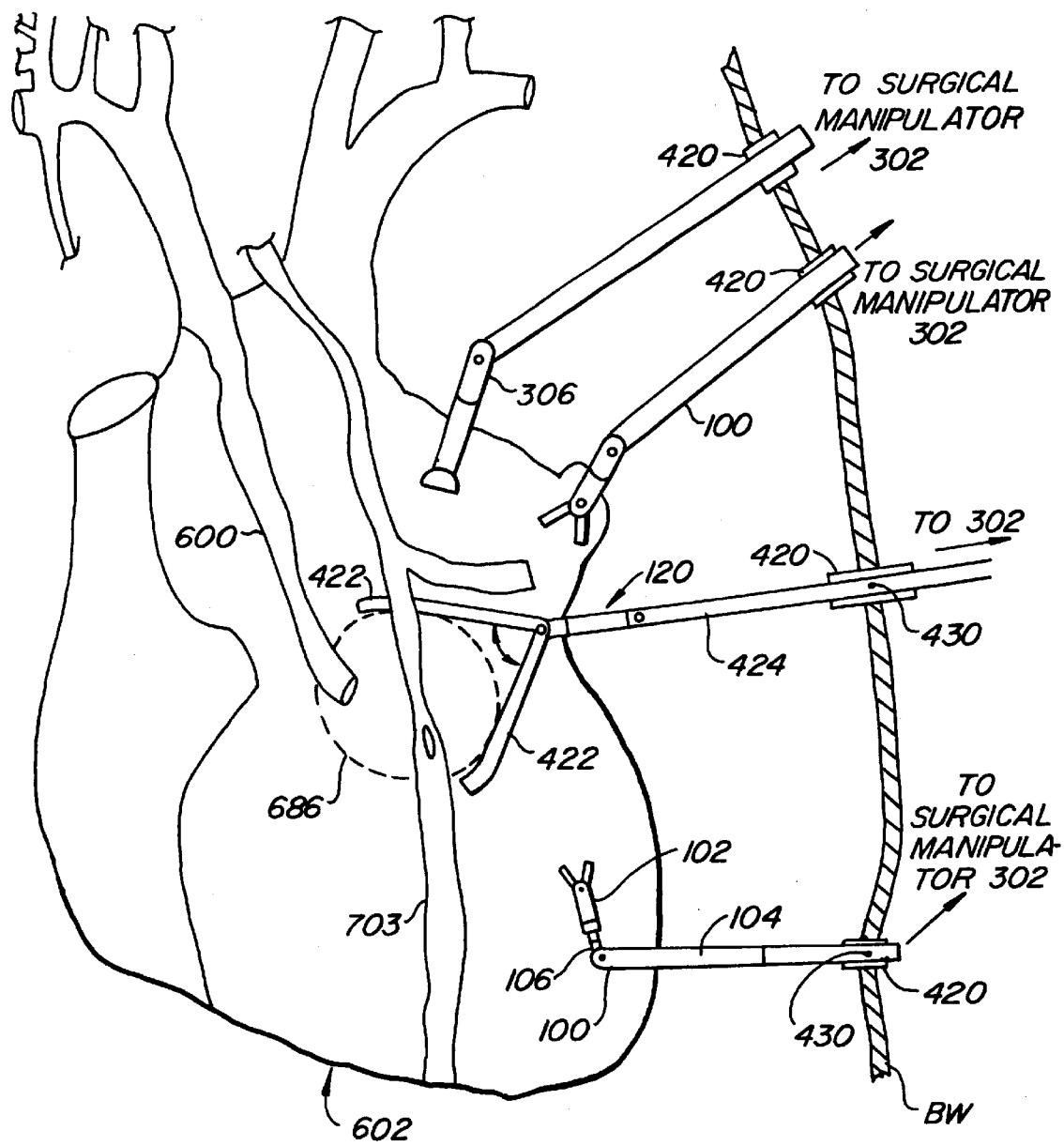
FIG. 13 shows a schematic view of a surgical cardiac worksite illustrating an arrangement of end effectors of surgical manipulators and an endoscope for producing a telepresence effect, and an attachment assembly comprising a servomechanism-operated manipulator arm including a bifurcated attachment member, with six degrees of freedom of movement, for at least partially immobilizing movement of the cardiac worksite.

Referring to FIG. 13, the coronary artery bypass grafting procedure will generally proceed by manipulating surgical tools 100 through a body wall BW, such as the chest wall, abdominal wall, or like, while the tools are inserted through the body wall BW using cannulas 420. Manipulator 302 supporting stabilizer 120 stabilizes motion of surgical worksite 686 by applying force to the stabilizer (here with a V-shaped arrangement of linear design attachment members 422) through downward pressure or tensioning of internal cables such that the stabilizer inhibits motion of the surgical worksite 686 in at least one direction, and ideally in a plurality of directions. As explained more fully in co-pending U.S. patent application Ser. No. 09/436,982 filed concurrently herewith, the full disclosure of which is incorporated herein by reference, residual motion of surgical worksite 686 may optionally be accommodated by the robotic surgical system by tracking the remaining motion and maintaining alignment between the surgical tools 100 and the movement of the surgical worksite. Advantageously, the heart may be tolerant of the forces involved in reducing motion of the surgical worksite as compared to attempts to completely cease motion.

As was generally described above, tools 100 may be positioned by pivoting the tools about insertion points 430 through body wall BW by axial movement along the tool shafts through the cannulas 420, rotation of the shafts about their axes, and articulation of the tools. In some embodiments endoscope 306 may have a fixed viewing angle rather than being an articulated structure as illustrated in FIG. 13.

Figure 14A:
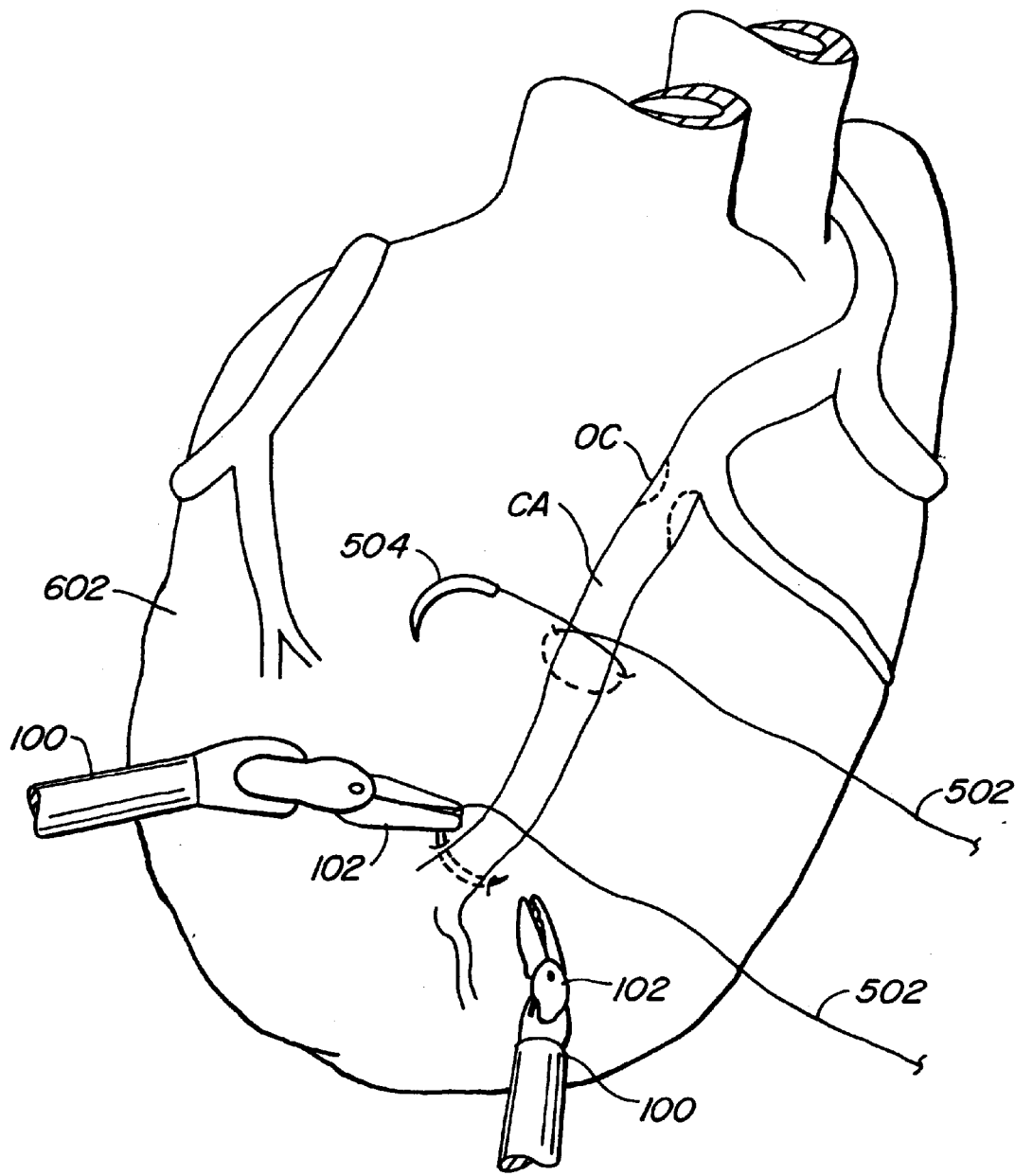
FIGS. 14A and 14B illustrate a method for using the stabilizer of FIG. 9 to stabilize a target region of the heart and also to isolate a target region of a coronary artery for anastomosis.
Figure 14B:
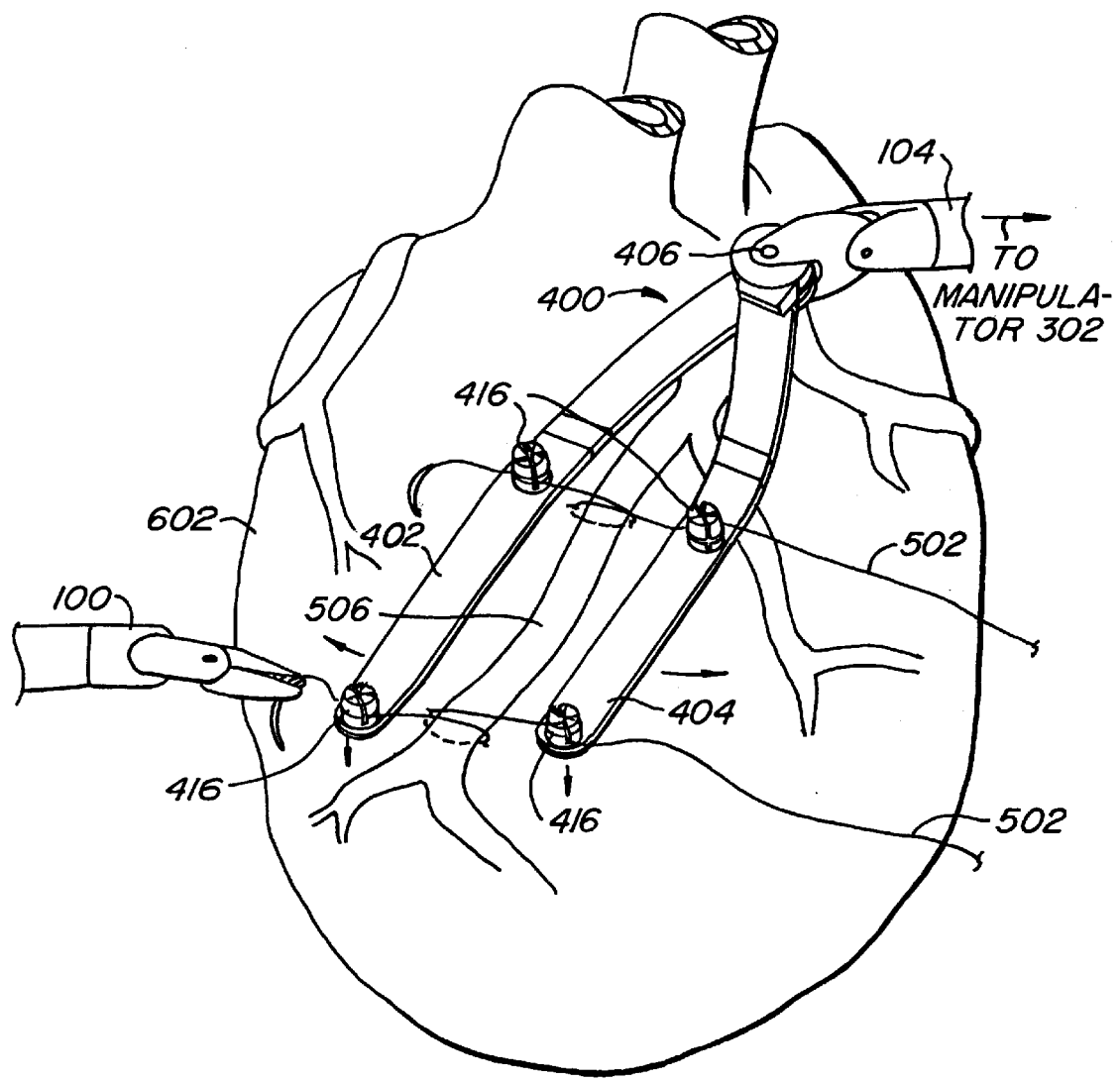

A method for isolating a coronary artery CA downstream of an occlusion OC using preferable stabilizer 400 can be understood with reference to FIGS. 14A and 14B. Rather than straightening and tensioning coronary artery CA by tensioning elastic flexible members through the chest wall, a flexible member 502 is passed under and around the coronary artery CA using end effectors 102 of tools 100 as illustrated in FIG. 14A. Stabilizer 400 is positioned against heart 602 with the first and second bodies 402, 404 of the stabilizer positioned on either side of the coronary artery CA so as to inhibit motion of the surgical worksite. A target region 506 of the coronary artery CA is isolated from upstream and downstream blood flow by tensioning flexible member 502 and tying the tensioned flexible members off to anchors 416 of stabilizer 400. Tying off the vessel in this manner not only permits isolation of the surgical site, but also can help to inhibit movement of the surgical worksite between bodies 402, 404 during beating-heart surgery.

The exemplary embodiment flexible member 502 comprises silastic tubing, the tube preferably being large enough to catch in the channels of anchors 416 but not so large as to require large penetrations about the vessel or to be ineffective in occluding the vessel. For the exemplary anchors 416 having a channel with a width of about 0.010 inches, a preferred silastic tubing will have an outer diameter of about 0.050" and an inner diameter of 0.030", such as that available from Quest Medical of Allen, Tex. under the product name "Retract-O-Tape". Alternative elastic and inelastic flexible members may also be used. Flexible member 502 is tied off to anchors 416 using tools 100 in a totally endoscopic procedure, while heart 602 is beating and without any need for a thoracotomy or a mini-thoracotomy.

Figure 14C:
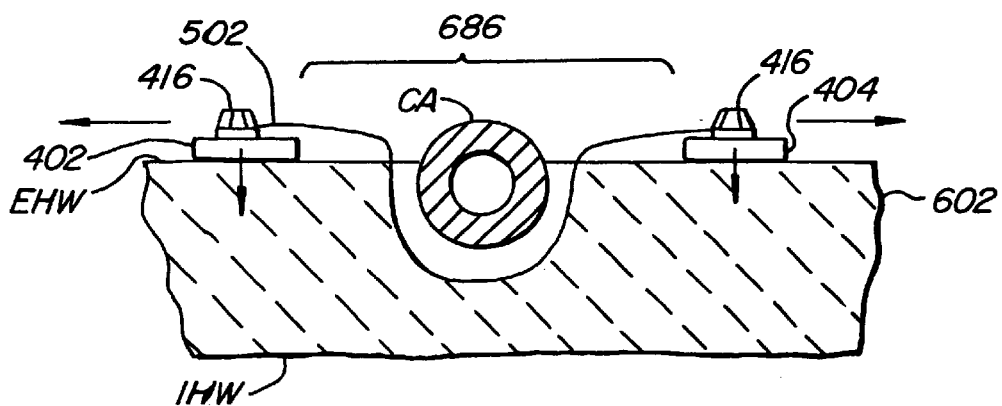
FIG. 14C schematically illustrates an alternative preferred arrangement of the flexible members anchored to the bifurcated stabilizer bodies to isolate the target region of a coronary artery in the method of FIGS. 14A and 14B.

Referring now to FIG. 14C, an alternative arrangement for occluding coronary artery CA using preferred stabilizer 400 is illustrated. It should be understood that tensioning of flexible member 502 may be effected by moving first body 402 away from second body 404 about pivot 406, or the flexible member may simply be tied with tension to the pre-positioned anchor of the stabilizer using tools 100. Regardless, tension of flexible member 502 will preferably substantially occlude the lumen of coronary artery CA, and the tension may also help to inhibit movement of the coronary tissues between first and second bodies 402, 404. As shown in FIG. 14C, the tubing is preferably passed sufficiently under the artery CA to capture some of the heart tissue between an exterior heart all surface EHW and an interior heart wall surface IHW so as not to tear or damage either the vessel or the heart when the flexible member is pulled taught.

Figure 15A:
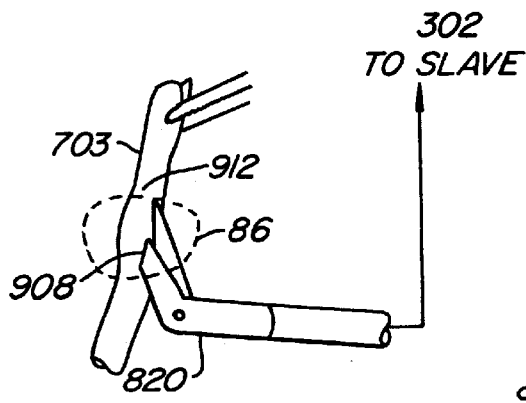
FIGS. 15A–D shows schematic views illustrating the use of surgical manipulators of the robotic surgical system of FIG. 1 to suture an anastomosis on a beating heart.
Figure 15B:
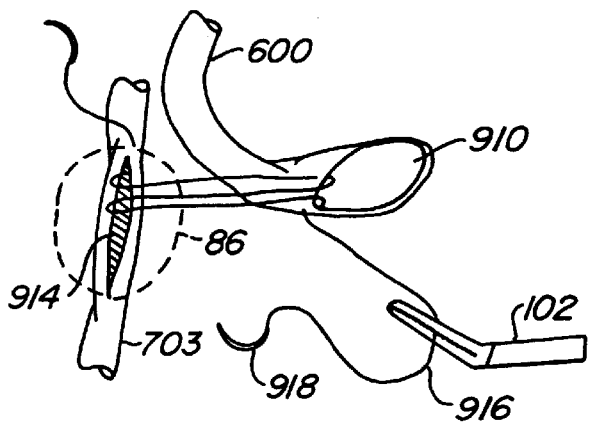
Figure 15C:
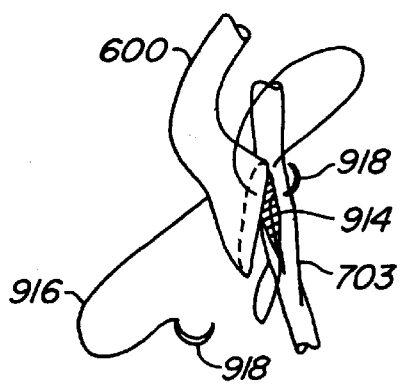
Figure 15D:
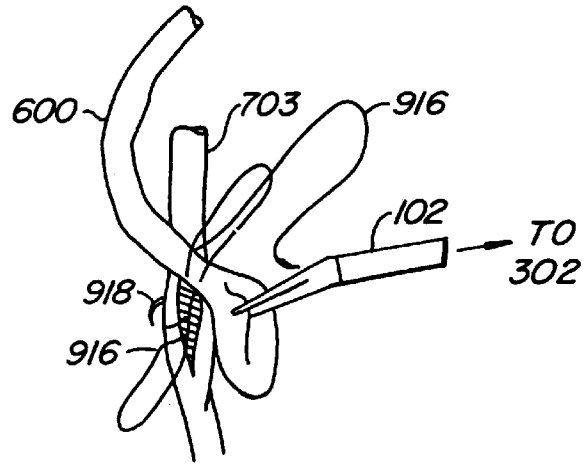

Referring now to FIG. 15A, the surgical worksite 86 is seen. An incision 908 is made in the wall of the coronary artery 703, where the incision 908 has dimensions selected to match those of the upstream free end 910 (see FIG. 15B) of the internal mammary artery 600 graft. The incision 908 is made by first piercing the arterial wall 912 using the tip of a scalpel (not illustrated). The surgical instrument 82c, such as a scissor, is attached to the surgical manipulator 78. The surgical tool 82c is introduced through the incision 908 to axially extend the incision 908, as illustrated at 914 in FIG. 15B. The movement of surgical instrument 82c is directed by the surgeon from the surgeon interface 250 (see FIG. 3A).

The internal mammary artery can be joined to the extended incision 914 in the coronary artery 703 by a variety of conventional techniques, including suturing, laser welding, microstapling, and the like. It will be preferred to use conventional suturing techniques as illustrated in FIGS.

15A–D. A length of suture 916 (see FIGS. 15A–D) has needles 918 at either end, which are manipulated using the forceps 82d attached to the surgical manipulator 80 to join the free upstream end 910 of the internal mammary artery 600 graft to the opening created by extended incision 914 in the coronary artery 703.

After the suturing is complete, the internal mammary artery 600 will be joined to the coronary artery 703. It is noted that prior to suturing, temporary clips (not shown) are placed upstream and downstream of the region of the internal mammary artery to be transected. After suturing, the temporary clips will then be removed to permit blood flow into the coronary artery 703, thus bypassing the previous blockage in the coronary artery 703. The downstream free end of the internal mammary artery will remain clipped as before. Following completion of the coronary anastomosis, all heart manipulating devices (not shown) will be removed from the patient, and the heart will be permitted to return to its natural orientation.

Figure 16:
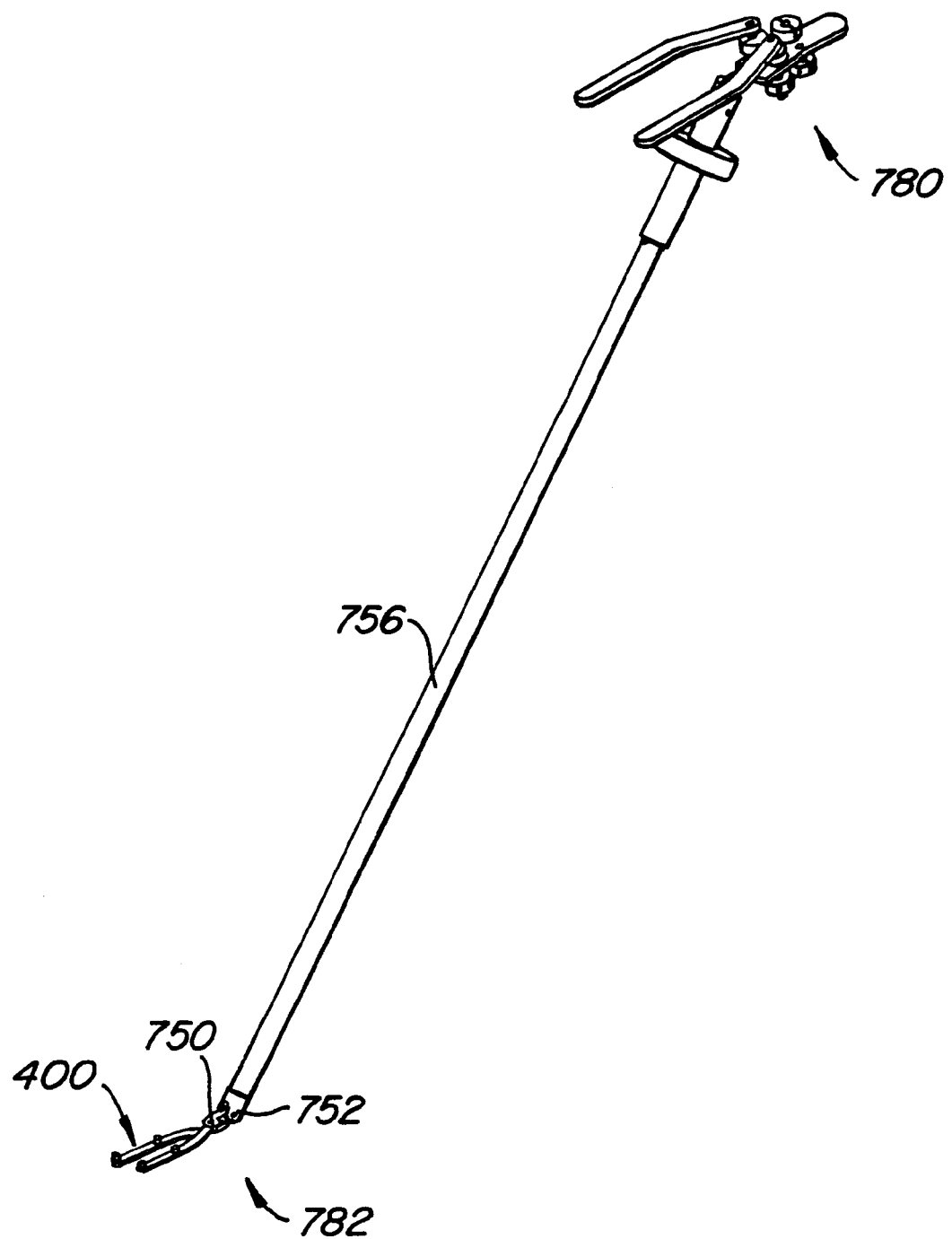
FIGS. 16 and 17 show a preferred mechanism for manually manipulating the stabilizer from outside the patient's body.
Figure 17:
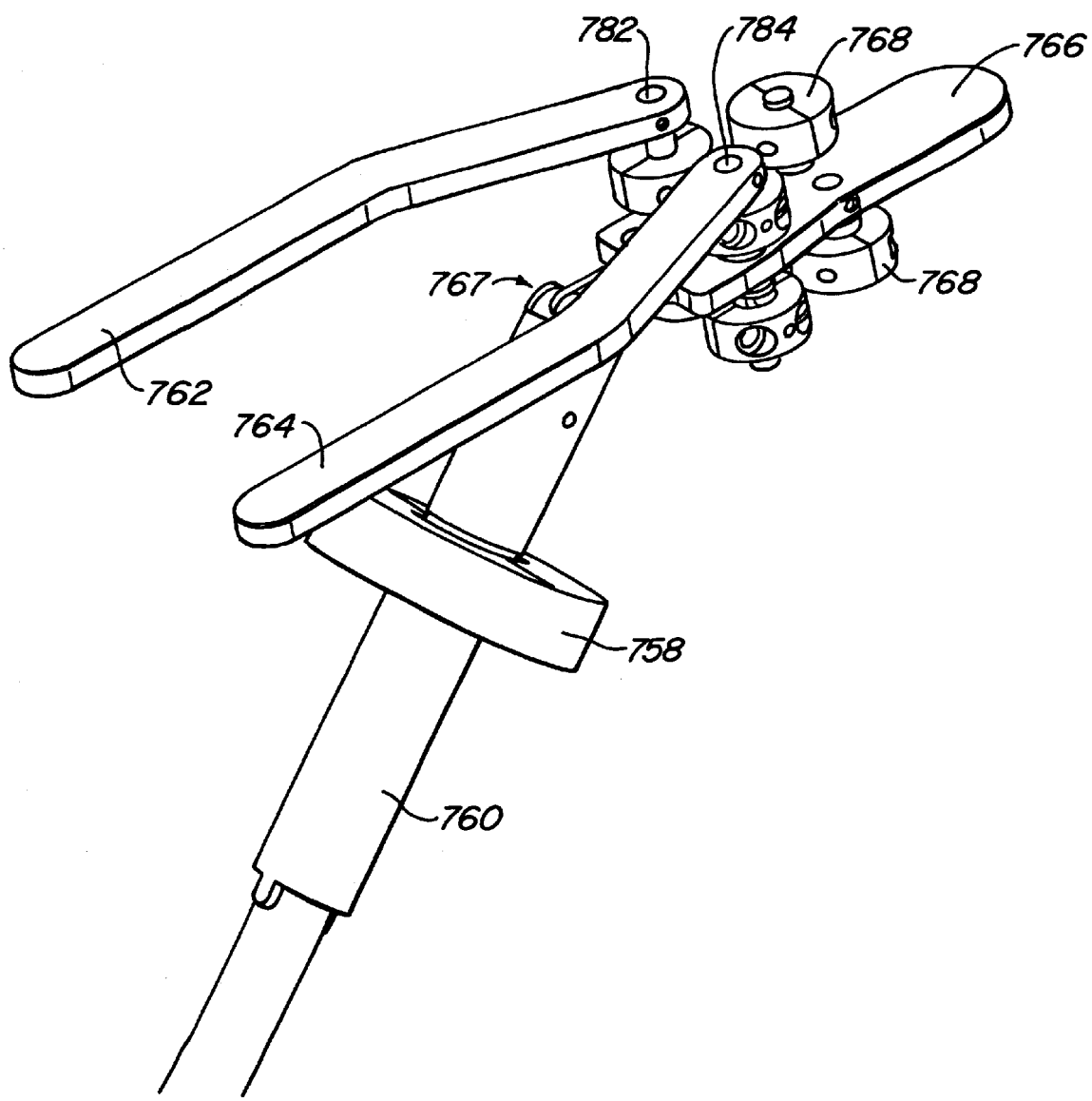

FIGS. 16 and 17 depict schematic views of a preferred embodiment of a retractor that can be manually manipulated by a surgeon's assistant during a surgical procedure. This manually operable retractor comprises a longitudinal shaft 756 coupling the distal end 782—preferably comprising the stabilizer end effector 400 and the proximal and distal devises 752 and 750—to the proximal, manually manipulable end 780. As shown in FIG. 17, the proximal end 780 generally comprises a back-end clevis 760, pitch plate 766, and back-end grips, 762 and 764. The back-end clevis 760 provides the interface between the back-end and the shaft 756. The pitch plate 766 rotates with respect to the back end clevis around axis 767 and is operatively coupled to the distal clevis so that its movement around axis 767 relative to the back-end clevis causes substantially similar movement of the distal clevis 750 around axis 754 relative to the proximal clevis 752. Grips 762 and 764 are attached to the pitch plate 766 and rotate with respect thereto around axes 782 and 784 that are preferably substantially perpendicular to the pitch axis.

The elongate shaft or coupling tube 756 houses cable/hypotube assemblies operatively connecting the proximal and distal ends of the apparatus. The shaft permits the distal end 782, which may be inside the body, to be manipulated by the proximal end 780, which typically remains outside the body in a minimally invasive procedure. The right-hand grip 762 is operatively coupled to the right-hand body 402; the left-hand grip 764 is operatively coupled to the left-hand body 404. Each operative coupling comprises a pair of opposed cable/hypotube assemblies for transmitting movement at the proximal end to the apparatus' distal end, so that each body/clevis may move in opposing directions around its corresponding pivot axis.

Although in the preferred embodiment, each body has a corresponding grip on the apparatus' proximal end, the manual controls may also comprise a single member operatively coupled to both bodies 402 and 404 so that movement of the single member at the proximal end of the apparatus moves both bodies relative to the shaft but not relative to one another. This single member preferably would comprise an actuating mechanism for opening and closing the bodies relative to one another. With this combination of controls, the same functionality as that achieved by the proximal end of the embodiment shown in FIG. 17 would be achieved.

The proximal end 780 also includes tensioning disks 768 that are used to introduce tension in the cable assemblies. Tension is typically provided during the manufacturing process, so all motion in one grip, for example, is transmitted to its corresponding distal body. Preferably, no motion is lost due to looseness in the cables.

Locking mechanism, comprising lock nut 758, can be releasably manipulated to prevent further motion of the cable/hypo-tube assemblies relative to shaft 756. This locking mechanism may be constructed so that the user can partially loosen the nut and adjust one degree of freedom of movement of the end effector while maintaining at least one other degree of freedom of movement substantially fixed.

Figure 17A:
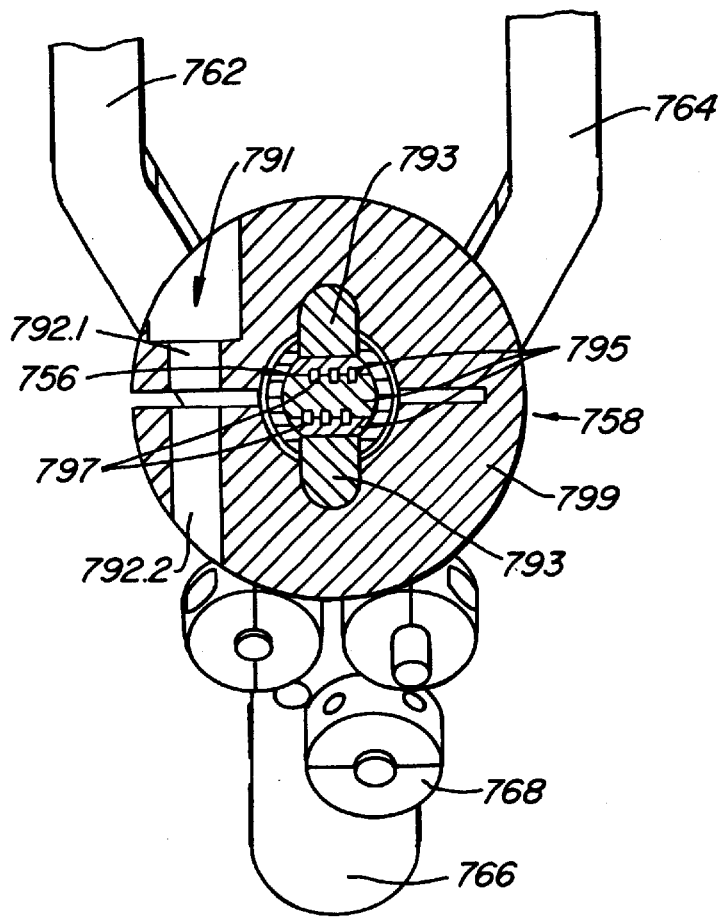
FIGS. 17A and 17B show partial schematic and cross-sectional views of the locking mechanism shown in FIG. 17.
Figure 17B:
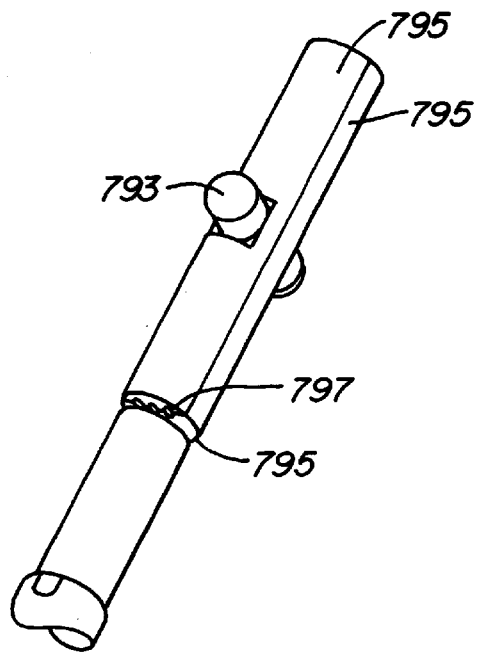

FIGS. 17A and 17B depict the locking mechanism 758 in more detail. A screw or threaded lever (not shown) is positioned within threaded channels 792.1 and 792.2 and may be used to tighten the two joined halves of clamp 799 around the centrally located mechanism shown best in FIG. 17A. If a screw is used, the screw head is held in recess 791. Tightening clamp 799 in this manner causes pins 793 to force locking plates 795 closer together, thereby increasing the friction between the locking plates 795 and the hypotube/cable assemblies 797 and so holding the assemblies in place.

The compression of clamp 799 is released by releasing the screw or threaded lever to allow the clamp halves to bias apart. Partially releasing the clamp in this manner maintains friction on the cable assemblies to continue to hold them in place, but also applies sufficiently less friction that each degree of freedom of movement of the distal portion of the instrument may be independently manipulated by overcoming the remaining friction applied by the clamp. In this way, the positioning of the instrument may be fine-tuned by manipulating (e.g., only one set of cables) without having to reposition the entire mechanism in all its degrees of freedom of movement.

In use, this manual instrument control mechanism may be held by the user or attached with a frame to the patient or the operating table, to maintain its position relative to the patient during the surgical procedure. For example, a positioning arm could attach to the rails of the operating table and a clamp could adjustably rigidly hold the shaft in position during the surgery. Preferably before clamping, the retractor 400 is straightened and inserted into the body through a cannula. When inside the body, the tool is manually manipulated into position. The user—typically the surgeon's assistant—stands next to the patient and watches the motion of the tool on a displayed image captured by an endoscope, for example. All of the motion is preferably scaled one-to-one, so that the surgeon can learn the position of the retractor bodies simply by viewing the relative positions of the proximal grips. Once the tool is in position, the position of the tool is fixed relative to the patient and the locking mechanism is tightened. Although this mechanism is disclosed in the context of a heart stabilizer, it has application to control any surgical end effector with a wrist joint and/or three degrees of distal freedom of movement. For example, the apparatus could be used to position a forceps around a piece of tissue, and then have the forceps hold that tissue until manually maneuvered to do otherwise. The application of this manually adjustable apparatus thus should not be understood as being limited to positioning a stabilizer.

Figure 18:
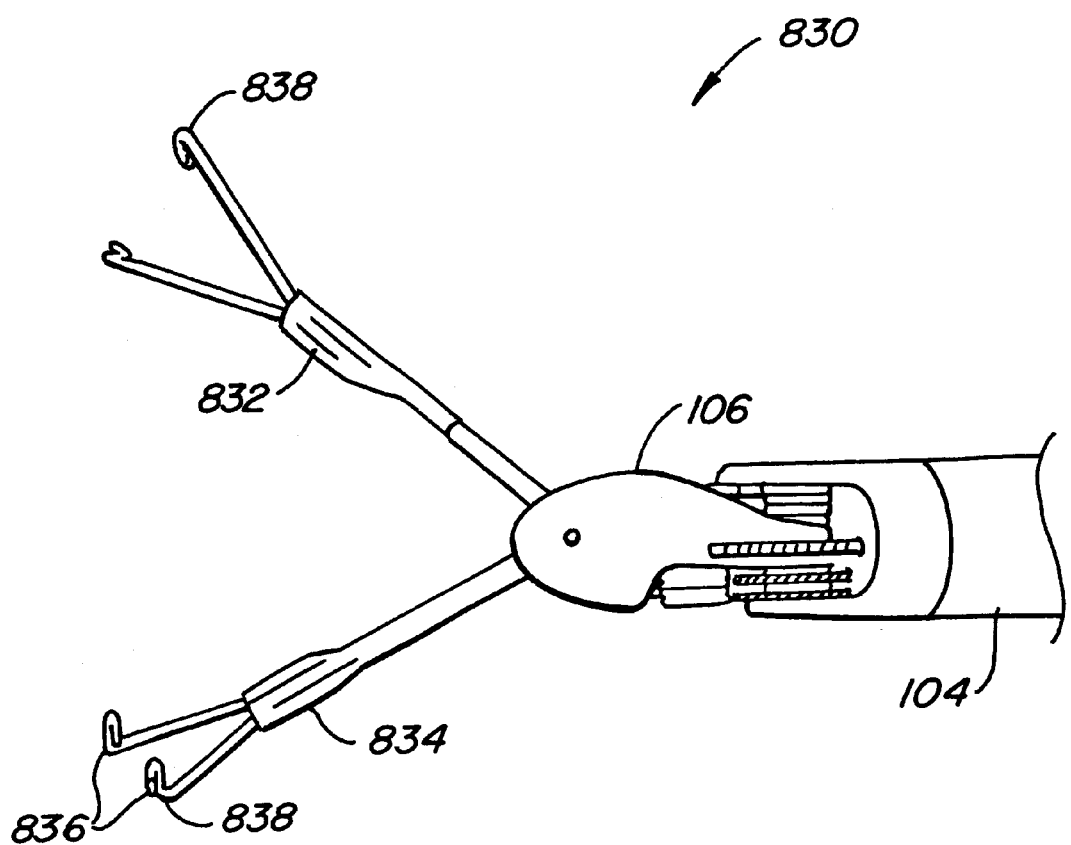
FIGS. 18 and 18A show a retractor for use with the system of FIG. 1.
Figure 18A:
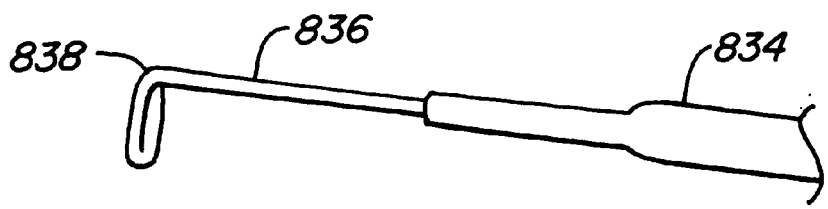

FIGS. 18 and 18A illustrate a robotic tissue retractor 830 for use with the system of FIG. 1. Retractor 830 includes first and second retractor elements 832, 834 which can be independently articulated, as described above. Each retractor element has at least one arm 836 with a bend 838 so that the arms can each pull and/or push tissue normal to the retractor element. Preferably, two or more arms are provided on each element, with the tool typically having one, two, or more retractor elements.

In use, retractor elements 832, 834 may be spread apart and used to retract tissue from an internal surgical site as described. The arms 836 of a first retractor element 832 may extend distally beyond bends 838 of the second retractor element 834 to avoid interference when the elements are aligned in a small profile configuration for insertion and removal. The exemplary retractor elements comprise flattened hypotube crimped and glued around formed wire, such as 0.021" diameter stainless. The proximal ends of the hypotube may similarly be crimped and glued to end effector elements of a microforceps or the like. Alternative retractor elements may comprise structures similar to those described in U.S. Pat. No. 5,613,937, the full disclosure of which is incorporated herein by reference.

Thus, while the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention, but that the invention will include all embodiments and equivalents falling within the scope of the appended claims.

What is claimed is:

1. A tissue stabilizer for use with a robotic surgical system to treat a target tissue within a patient body, the robotic surgical system having a plurality of manipulators with actuators for moving surgical end effectors in response to inputs by a system operator into an input device, the tissue stabilizer comprising:

a shaft having a proximal end and a distal end;

a first stabilizer body having a stabilizing surface adapted to engage and inhibit movement of the target tissue;

a joint coupling the distal end of the shaft to the stabilizer body;

a drive system drivingly coupled to the joint so that the stabilizer body can be moved relative to the shaft from outside the patient body; and a flexible element extending from the first stabilizer body to a second stabilizer body, the flexible element tensionable by moving the first stabilizer body away from the second stabilizer body using the drive system.

2. A surgical stabilizer system for inhibiting motion of a tissue at a surgical site, wherein a surface bordering the tissue is accessible at the surgical site, the system comprising:

a first body having a first anchor and a first stabilizing surface adapted to engage the tissue surface to inhibit motion of the tissue;

a second body having a second anchor and a second stabilizing surface adapted to engage the tissue surface to inhibit motion of the tissue, the second body being movable relative to the first body; and a flexible tension member attachable to the first anchor and to the second anchor to engage the tissue between the first and second tissue stabilizing surfaces, wherein the first body is coupled to the second body by a joint, the joint maintaining substantial alignment between the first and second stabilizing surface for concurrent engagement against the tissue surface and wherein movement of the first anchor away from the second anchor tensions the flexible member and can urge the flexible member against the tissue.

3. A surgical stabilizer system for inhibiting motion of a tissue at a surgical site, wherein a surface bordering the tissue is accessible at the surgical site, the system comprising:

a first body having a first anchor and a first stabilizing surface adapted to engage the tissue surface to inhibit motion of the tissue;

a second body having a second anchor and a second stabilizing surface adapted to engage the tissue surface to inhibit motion of the tissue, the second body being movable relative to the first body;

a flexible tension member attachable to the first anchor and to the second anchor to engage the tissue between the first and second tissue stabilizing surfaces; and another tension member spanning from a third anchor on the first body to a fourth anchor on the second body, movement of the bodies apart tensioning both the flexible members to urge the tension members against the tissue.

4. The stabilizer of claim 3, the tissue comprising a target region of a blood vessel, wherein the flexible members extend laterally across the blood vessel so that the tension occludes the vessel and isolates the target region between the flexible members.

5. The stabilizer of claim 4, further comprising a needle attached to an end of the flexible member, the flexible member comprising suture or Silastic tubing.

6. A surgical stabilizer system for inhibiting motion of a tissue at a surgical site, wherein a surface bordering the tissue is accessible at the surgical site, the system comprising:

a first body having a first anchor and a first stabilizing surface adapted to engage the tissue surface to inhibit motion of the tissue;

a second body having a second anchor and a second stabilizing surface adapted to engage the tissue surface to inhibit motion of the tissue, the second body being movable relative to the first body; and a flexible tension member attachable to the first anchor and to the second anchor to engage the tissue between the first and second tissue stabilizing surfaces, wherein the first anchor comprises a channel that laterally receives the flexible member to affix the flexible member to the anchor.

7. The stabilizer of claim 6, wherein the anchors protrude from the bodies away from the tissue engaging surfaces.

8. The stabilizer of claim 7, wherein the first and second bodies are coupled at a proximal joint, and wherein the first anchor is disposed distally beyond a distal end of the second anchor to avoid interference when the bodies overlap for insertion into the internal surgical site.

9. A surgical stabilizer system for inhibiting motion of a tissue at a surgical site, wherein a surface bordering the tissue is accessible at the surgical site, the system comprising:

a first body having a first anchor and a first stabilizing surface adapted to engage the tissue surface to inhibit motion of the tissue;

a second body having a second anchor and a second stabilizing surface adapted to engage the tissue surface to inhibit motion of the tissue, the second body being movable relative to the first body;

a flexible tension member attachable to the first anchor and to the second anchor to engage the tissue between the first and second tissue stabilizing surfaces;

a pivotal joint coupling the first and second bodies;

a shaft having a proximal end and a distal end;

a wrist joint coupling the shaft to the bodies to provide at least one degree of freedom of movement of the stabilizing surfaces relative to the shaft; and a robotic actuation interface disposed at the proximal end of the shaft and a drive system coupling the interface to the joints for actuation of the stabilizer with motors of a robotic manipulator.

10. A tissue stabilizer for use with a robotic surgical system to treat a target tissue within a patient body, the robotic surgical system having a plurality of manipulators with actuators for moving surgical end effectors in response to inputs by a system operator into an input device, the tissue stabilizer comprising:

a shaft having a proximal end and a distal end;

a first stabilizer body having a stabilizing surface adapted to engage and inhibit movement of the target tissue;

a joint coupling the distal end of the shaft to the stabilizer body;

a wrist assembly coupling the stabilizer body to the shaft, the wrist assembly providing the stabilizer body first and second degrees of freedom relative to the shaft; and a drive system drivingly coupled to the joint so that the stabilizer body can be moved relative to the shaft from outside the patient body, wherein the drive system comprises first and second drive elements movable relative to the shaft by the actuators to effect movement of the stabilizer body along the first and second degrees of freedom.

* * * * *